United States Patent
Yumoto et al.

(10) Patent No.: US 7,573,921 B2
(45) Date of Patent: Aug. 11, 2009

(54) LASER LIGHT SOURCE

(75) Inventors: Junji Yumoto, Atsugi (JP); Osamu Tadanaga, Zama (JP); Masaki Asobe, Isehara (JP); Hiroyuki Suzuki, Tokyo (JP); Kaoru Yoshino, Atsugi (JP); Hiroshi Miyazawa, Isehara (JP); Yoshiki Nishida, Mito (JP); Hirohisa Kanbara, Isehara (JP); Tsutomu Yanagawa, Isehara (JP); Eishi Kubota, Isehara (JP); Hiroyasu Mawatari, Isehara (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 11/839,409

(22) Filed: Aug. 15, 2007

(65) Prior Publication Data
US 2007/0297465 A1    Dec. 27, 2007

Related U.S. Application Data

(62) Division of application No. 10/531,485, filed as application No. PCT/JP2004/010947 on Jul. 30, 2004, now Pat. No. 7,391,795.

(30) Foreign Application Priority Data

| Aug. 1, 2003 | (JP) | ............................. 2003-285383 |
| Aug. 29, 2003 | (JP) | ............................. 2003-308034 |
| Oct. 8, 2003 | (JP) | ............................. 2003-350018 |
| Nov. 6, 2003 | (JP) | ............................. 2003-377351 |

(51) Int. Cl.
*H01S 3/10*    (2006.01)
(52) U.S. Cl. ............................. 372/22; 372/20; 372/23
(58) Field of Classification Search ............. 372/21–23
See application file for complete search history.

(56) References Cited

U.S. PATENT DOCUMENTS

| 5,012,478 A | | 4/1991 | Hattori et al. |
| 5,036,220 A | | 7/1991 | Byer et al. |
| 5,341,388 A | * | 8/1994 | Masuda et al. ................. 372/36 |

(Continued)

FOREIGN PATENT DOCUMENTS

EP    0 287 880 A1    10/1988

(Continued)

OTHER PUBLICATIONS

K. Kubo et al., *Spin and Polarization*, Baifukan, Oct. 31, 1994, pp. 21-24 (with English translation).

(Continued)

*Primary Examiner*—Minsun Harvey
*Assistant Examiner*—Xnning Niu
(74) *Attorney, Agent, or Firm*—Workman Nydegger

(57) ABSTRACT

A laser light source is disclosed consisting of first and second lasers that respectively generate laser beams of wavelengths $\lambda_1$ and $\lambda_2$. Wavelength $\lambda_1$ is in the range of 0.9-1.0 μm. A nonlinear optical crystal uses the laser beams of wavelengths $\lambda_1$ and $\lambda_2$ as inputs, and outputs a coherent beam having a wavelength $\lambda_3$ of a difference frequency that satisfies a relationship of $1/\lambda_1 - 1/\lambda_2 = 1/\lambda_3$. The nonlinear optical crystal has a periodically poled structure of a single period. The wavelength $\lambda_3$ of the difference frequency varies between 3.1 μm and 2.0 μm when the wavelength $\lambda_2$ varies between 1.3 μm and 1.8 μm.

7 Claims, 27 Drawing Sheets

U.S. PATENT DOCUMENTS

| | | | |
|---|---|---|---|
| 5,767,519 | A | 6/1998 | Gelbwachs |
| 5,796,764 | A * | 8/1998 | Corsini et al. ............... 372/6 |
| 5,911,018 | A * | 6/1999 | Bischel et al. ............... 385/16 |
| 6,738,397 | B2 | 5/2004 | Yamamoto et al. |
| 2003/0123498 | A1 | 7/2003 | Ishino |
| 2004/0027648 | A1 * | 2/2004 | Furukawa et al. ............ 359/328 |
| 2004/0086005 | A1 * | 5/2004 | Kitaoka et al. ............... 372/25 |

FOREIGN PATENT DOCUMENTS

| | | |
|---|---|---|
| JP | 63-262626 | 10/1988 |
| JP | 4-507299 | 12/1992 |
| JP | 6-175180 | 6/1994 |
| JP | 6-194343 | 7/1994 |
| JP | 2001-154068 | 6/2001 |
| JP | 2002-139428 | 5/2002 |

OTHER PUBLICATIONS

Harold J. Metcalf et al., *Laser Cooling and Trapping*, table, Springer, 1999, pp. 274.

George Patterson et al., *Fluorescent Protein Spectra*, Journal of Cell Science, No. 114, vol. 5, 2001, pp. 837-838.

Arkady F. Fradkov et al., *Far-red Fluorescent Tag for Protein Labelling*, Journal of Biochem, No. 368, 2002, pp. 17-21.

Dmitriy M. Chudakov, et al., *Kindling Fluorescent Proteins for Precise in Vivo Photolabeling*, Technical Report, vol. 21, Feb. 2003, pp. 191-194.

Dirk Richter et al., *Development of an Automated Diode-Laser-Based Multicomponent Gas Sensor*, Applied Optics, vol. 39, No. 24, Aug. 20, 2000, pp. 4444-4450.

Ioulia B. Zotova et al., *Reductions of Threshold for a Mid-Infrared Optical Parametric Oscillator by an Intracavity Optical Amplifier*, Optics Letters, vol. 28, No. 7, Apr. 1, 2003, pp. 552-554.

Chih-Wei Hsu et al., *Broadband Infrared Generation with Noncollinear Optical Parametric Processes on Periodically Poled $LiNbO_3$*, Optics Letters, vol. 26, No. 18, Sep. 15, 2001, pp. 1412-1414.

A. Yariv, *Quantum Electronics*, Third Edition, Chapter 16.5, 1988, pp. 392-397.

Richard M. Schotland et al., *The Determination of the Vertical Profile of Atmospheric Gases by Means of a Ground Based Optical Radar*, Third Symposium on Remote Sensing of Environment, 1964, pp. 215-224.

M. H. Chou et al., *1.5 μm-Band Wavelength Conversion Based on Cascaded Second-Order Nonlinearity in $LiNbO_3$ Waveguides*, IEEE Photonics Technology Letters, vol. 11, No. 6, Jun. 1999, pp. 653-655.

Osamu Tadanaga et al., *Highly-damage-resistant Quasi-phase-matched Wavelength Converter Using ZnO-doped $LiNbO_3$*, Proceedings of the 15th Annual Meeting of Institute of Electrical and Electronic Engineers, Lasers and Electro-Optics Society, vol. 1, 2002 (IEOS2002), pp. 79-80.

H. Moosmuller et al., *Sum-frequency generation of Continuous-wave Sodium $D_2$ Resonance Radiation*, Optics Letters, vol. 22, No. 15, Aug. 1, 1997, pp. 1135-1137.

Toshitsugu Ueda et al., *Spectroscopic Detection of Gas Using Diode-Pumped Difference-frequency Generation*, Collection of Symposium Lecture Delivered by Measurement Automatic Control Institute, 2004, pp. 24-256 (with English translation).

Y. K. Sin et al., *Laterally Coupled InGaAsP/InP Distributed Feedback Lasers at 1.5 μm for Chemical Sensing Applications*, Electronics Letters, vol. 37, No. 9, Apr. 26, 2001, pp. 567-569.

D.K. Serkland et al., *Amplitude Squeezing by Means of Quasi-Phase-Matched Second-Harmonic Generation in a Lithium Niobate Waveguide*, Optics Letters, vol. 22, No. 19, Oct. 1, 1997, pp. 1497-1499.

A list of semiconductor lasers and their corresponding wavelength bands and other properties as available at time of preparing application and as identified as non-patent document 10 at pp. 19 and 27 of the filed English translation of the present application.

Semiconductor lasers and related properties, identified as non-patent document 10 in application, obtained from http//laserfocusworld.365media on Jun. 24, 2003.

Office Action dated Mar. 5, 2007 for U.S. Appl. No. 10/531,485 which relates to the same invention as the present application.

P.H. Chiu et al., *All-Solid-State Single-Mode Sum-Frequency Generation of Sodium Resonance Radiation*, Optics Letters, vol. 19, No. 24, Dec. 15, 1994, pp. 2116-2118.

D.M. Pennington et al., *Compact Fiber Laser Approach to Generating 589 nm Laser Guide Stars*, CLEO/Europe 2003 Conference (Jun. 2003), p. 730.

Malin Premaratne et al., *Stability Analysis of a Semiconductor Laser with Wavelength Dependent External-Mirror*, IEEE, Cat. No. 99EX379, vol. 2, XP-002432838 (1999), pp. 1325-1328.

Shinobu Ohara et al., *Performance Characteristics of Fiber Bragg Grating Stabilized 980nm Diode Laser Pumped Difference Frequency Generation as an Efficient Spectroscopic Source*, LEOS, vol. 2 (Nov. 2001), pp. 869-870.

Toshitsugu Ueda et al., *Spectroscopic Detection of Ammonia Using Diode-Pumped Difference-Frequency Generation*, Proceedings of the SPIE—The International Society for Optical engineering SPIE-Int. Soc. Opt. Eng USA, vol. 4268, 2001, pp. 21-25.

* cited by examiner

US 7,573,921 B2

LASER LIGHT SOURCE

CROSS-REFERENCE TO RELATED APPLICATIONS

This application is a divisional of U.S. patent application Ser. No. 10/531,485, filed Apr. 15, 2005, which is a nationalization of PCT Application No. PCT/JP2004/10947, filed Jul. 30, 2004, which claims priority to Japanese Patent Application Nos. 2003-285383 filed Aug. 1, 2003, 2003-308034 filed Aug. 29, 2003, 2003-350018 filed Oct. 8, 2003, and 2003-377351 filed Nov. 6, 2003, which are incorporated herein by reference.

FIELD OF THE INVENTION

This invention relates to a laser light source, and more specifically, to a laser light source for outputting a coherent beam of either a wavelength in the yellow color range or the sodium D-line wavelength efficiently using lasers and a non-linear optical crystal, a laser light source capable of tuning a laser beam in the wavelength band of 2-3 μm in the mid-infrared region, and a laser light source for outputting a laser beam of oxygen absorption lines existing at wavelengths of 759 nm to 768 nm.

BACKGROUND ART

Presently, the lasers that have been put into practical use are known to include gas lasers, such as the He—Ne laser and the Ar laser, solid state lasers, such as the Nd-YAG laser, dye lasers, and semiconductor lasers. FIG. 1 shows a relationship between wavelength band and output power of lasers. In recent years, compact, lightweight, and inexpensive semiconductor lasers have become popular in wavelength band 102 in the visible and infrared regions. Especially, in the optical communication filed, 1.3-μm band and 1.5-μm band semiconductor lasers for signal light sources and the 0.98-μm band and 1.48-μm band semiconductor lasers for fiber amplifier pumping have come into widespread use. Moreover, the semiconductor laser is used also as lasers for CD and red lasers, and the semiconductor laser is used also in wavelength band 101 in the visible and infrared regions used for reading and writing storage media, such as DVD and Blue-ray.

However, the semiconductor laser has not been put into practical use in wavelength band 111 of the green, yellowish green, and yellow ranges of wavelengths of 0.5-0.6 μm and in wavelength band 112 of the mid-infrared range 2-5 μm, and hence the gas laser and the solid-state laser, which are expensive and consume large electric power, are being used.

Optical characteristics, such as refractive index and absorption, of optical media of liquids, glasses, etc. have become important evaluation items to specify characteristics of optical instruments and to control qualities, such as accuracy and purity, of foods, medicines, etc. For measurement of these optical characteristics, the light source for generating the sodium D-line of wavelengths of 589-590 nm in the yellow range included in wavelength band 111 is being used.

For example, a relationship between the refractive index and the sugar content in a liquid is defined as Brix value by ICUMSA (International Commission for Uniform Methods of Sugars Analysis) and a method for finding the sugar content from measurement of the refractive index is provided. This method is applied to sugar content measurement of fruits and alcoholic beverage, being used widely industrially.

In the field of medicines, the Japanese pharmacopoeia defines refractive indices of solutions in which respective medical agents are solved as one of quality control measures of medical agents. There is a case where a "right-hand-system" medicine that has a spiral structure, such as thalidomide, may have a medicinal effect, but a "left-hand-system" medicine may serve as a poison. It is impossible to separate physicochemically substances each having mutually inverse spiral structure like this from each other. However, it is known that these substances exhibit different optical activities, and can easily be identified optically. Then, after phytotoxicity accidents like thalidomide, the Japanese pharmacopoeia defines a measurement of angle of rotation using the sodium D line. Medicines exhibiting such a property include a large number of medicines, such as menthol, prostaglandin, β lactam antibiotics, and quinolone antibacterial agents, besides thalidomide.

Presently, a laser light source for generating the sodium D line has not been realized, and a sodium vapor lamp or yellow LED is used as a light source. A light beam from a sodium vapor lamp is excellent in monochromaticity, but is a divergent light beam emitted in all directions. Therefore, it is difficult to collimate it, and so accurate measurement of optical characteristic is difficult. Moreover, since focused energy does not reach a high level, it is necessary to use a high-power lamp.

On the other hand, the spectral linewidth of the yellow LED is as wide as approximately 20 nm. Because of this, the spectral linewidth is intended to be narrowed by extracting a spectrum near the sodium D line using an optical filter, but there is a limit to narrow it. Moreover, since the yellow LED light lacks coherency, there is a limit in improving measurement accuracy.

In the context of such facts, improvement in accuracy of optical evaluation methods that have been prescribed with the sodium D-line wavelengths are being demanded in many industrial fields, such as quality control of foods and medicines. If a laser at the sodium D line can be realized, measurement using light interference will become possible. With the use of optical interference, measurement accuracy of the refractive index of various liquids and optical media including foods and medicines can be improved from the present value by about two orders of magnitude, and low consumption power and miniaturization become possible as well.

The electronic structure of sodium and characteristics of light generated from its energy transition will be described (see Non-patent document 1). It is known that wavelengths of emission from a sodium atom are 589.592 nm (D1 line) and 588.995 nm (D2 line). The D1 line and D2 line are collectively called D line, and the wavelength of D line may be called 589.3 nm, taking an average of the two wavelengths. FIG. 2 shows the energy levels of a sodium atom. The D line is generated accompanying a transition from the 3P level, which is the first excitation state, to the 3S level, which is the ground state. The 3P level has a fine structure of $3P_{1/2}$ and $3P_{3/2}$. Emission of the D1 line is caused by a transition from $3P_{1/2}$ to $3S_{1/2}$ and emission of the D2 line is caused by a transition from $3P_{3/2}$ to $3S_{1/2}$.

The $3S_{1/2}$, $3P_{1/2}$, and $3P_{3/2}$ levels have hyperfine structures due to interaction of the electron magnetic moment and the intrinsic magnetic moment of the atomic nucleus. The $3S_{1/2}$ level splits into two levels whose energy difference is 7.3 μeV, the $3P_{1/2}$ level splits into two levels whose energy difference is 0.78 μeV, and the $3P_{3/2}$ level splits into four levels whose energy difference is 0.48 μeV (maximum difference).

In order to realize a laser emitting light at the D1 line wavelength and the D2 line wavelength, it is necessary to create population inversions between energy levels corresponding to each light. In order to create a population inversion, it is necessary to construct a three-level system or four-level system. However, in the energy levels shown in FIG. 2, relaxation of $3P_{3/2}$ to $3P_{1/2}$ is a forbidden transition, and a relaxation time of $3P_{1/2}$ to $3S_{1/2}$ is 15.9 ns (Non-patent document 2). For example, when comparing it with a relaxation time of 3.2 μs in the $TiAl_2O_3$ laser, the former is shorter than the latter by two orders of magnitude or more. Therefore, it is difficult to create a population inversion between $3S_{1/2}$ and $3P_{1/2}$, so laser oscillation of the sodium D-line wavelength has not yet been realized. Alternately, although laser oscillation using the hyperfine structure is conceivable, the energy differences of the hyperfine structures of the $3S_{1/2}$, $3P_{1/2}$, and $3P_{3/2}$ levels in a sodium atom are about four orders of magnitude smaller than energy at room temperature (300K), 25.8 meV. Because of this, excitation at room temperature is distributed to the both split levels in the hyperfine structure almost equally, and cannot create a population inversion. For these reasons, lasers at the sodium D1 line and D2 line have not been realized until now.

Conventionally, semiconductor lasers have been put to practical use only in the wavelength bands of shorter than 500 nm and longer than 620 nm. In the wavelength band of 500-620 nm, solid-state lasers have been realized by a second overtone generation method using fiber lasers or the Nd-YAG laser, but a solid-state laser of an arbitrary wavelength has not yet been realized.

On the other hand, the second overtone generation method (SHG method) using a nonlinear crystal is known as a method for generating coherent light in the visible range. In order to generate light of the D1 line or D2 line by this method, light of the 1179.2-nm wavelength or the 1178.0-nm wavelength is required. Unfortunately, although these wavelengths can be attained by semiconductor lasers, it is extremely difficult to obtain a laser capable of delivering necessary power.

Visible light can also be obtained by generating sum frequency of two excitation laser beams with a nonlinear crystal. In this method, energy of sum frequency light is given by a sum of energies of the two excitation beams. This method comes with an advantage that freedom of a combination of wavelengths of the two excitation beams is widened because a desired wavelength is obtained by sum frequency generation. Therefore, it is the most practical method to realize a laser of an arbitrary wavelength. However, generally nonlinear optical phenomena had a problem of low efficiency. In order to solve this problem, selection of an existing laser device that can deliver high excitation light intensity and that is compact and consumes low electric power as well as improvement in characteristics of a nonlinear optical crystal become important.

The first object of this invention is to provide a laser light source that generates a coherent beam that is energy-efficient with a narrow linewidth and excellent directivity and generates a coherent beam of a wavelength of the sodium D line.

Conventionally, the laser microscope that scans a sample with a confocal laser beam to obtain an optical tomogram is known. The laser microscope is being used for analyzing distributions of a substance with fluorescent labeling in a tissue and cell. Moreover, there is known a flow cytometer that irradiates a laser beam onto a stream of cells aligned in a line, and analyzes and isolates a cell preparatively depending on fluorescence intensity. The flow cytometer is a measuring apparatus that uses a flow cytometry method for identifying a cell qualitatively using properties of a cell, for example, a size, a DNA content, etc. as optical parameters.

Although the fluorochrome is used as fluorescent labeling in recent years, since the fluorochrome was a foreign matter for cells, there are problems that the properties of a cell is affected, a cell dies, etc. Therefore, the method for performing fluorescent labeling with a green fluorescent protein extracted from jellyfish etc. is being used. Moreover, fluorescent proteins that exhibit florescence of yellow and red have been obtained by mutation and genetic manipulation of green fluorescent proteins (for example, see Non-patent document 3), and more detailed measurement and analysis are being conducted using multicolor fluorescence.

Since the red fluorescent protein has the absorption maximum at wavelengths of 560-590 nm (for example, see Non-patent document 4), a laser light source having an oscillation wavelength in this wavelength band is expected. Since lasers having oscillation wavelengths in this wavelength band are only large-sized lasers, such as a dye laser; a 532-nm solid-state laser and a 543-nm He—Ne laser are being used instead. However, since at these wavelengths, fluorescence wavelengths of green fluorescent proteins and absorption wavelengths of yellow fluorescent proteins overlap remarkably, these are inconvenient for measurement and analysis using multi-color fluorescent proteins.

Very recently, there is reported Kindling red fluorescent protein that emits red fluorescence stably for a long time of more than 72 hours by irradiation of intense green laser beam (wavelengths of 530-560 nm) (for example, see Non-patent document 5). An effect that the use of Kindling-Red fluorescent protein enables long-time observation of how a cell divides using fluorescence and other effects are expected. However, with the conventional 532-nm solid state laser and the 543-nm He—Ne laser, overlap between the fluorescence wavelengths of green fluorescent proteins and the absorption wavelengths of yellow fluorescent proteins is are significant. Therefore, realization of a compact solid-state laser having an oscillation wavelength as close to 560 nm as possible is desired.

Moreover, metalloporphyrin is a molecule contained in a protein that bears an important function for life activity of animals and plants, such as photosynthesis and respiratory metabolism, having an absorption maximum near the 590-nm wavelength. Since these emission wavelengths of metalloporphyrin exhibit peaks near 600 nm, if a laser of the 589-nm wavelength is used, overlap with the emission wavelengths is too large to perform measurement. Consequently, a golden yellow laser of the 585.0-nm wavelength is needed.

Furthermore, the 546.1-nm wavelength (yellowish green) corresponding to one of emission lines (e-line) emitted from a mercury vapor lamp is a wavelength at which human's visibility is highest, being used as a wavelength of the refractive index standard for optical glasses. As shown in FIG. 1, in the green, yellowish green, yellow ranges of 500-600 nm included in wavelength band 111, efficient and highly stable laser light sources are needed.

However, as described above, semiconductor lasers have been put to practical use only in the wavelength bands of shorter than 500 nm and longer than 620 nm. In the wavelength band of 500-620 nm, a solid-state laser of an arbitrary wavelength has not yet been realized. In order to generate light in the yellow range by the SHG method, a light source of a wavelength of 1092.2 nm, 1120.0 nm, or 1170.0 nm is needed. However, although the semiconductor lasers can oscillate at these wavelengths, it is very difficult to obtain a laser capable of delivering necessary output.

As described above, in making use of nonlinear optical phenomena, it is very important to select an existing laser that can deliver high excitation beam intensity and that is compact and consumes low power as well as improving the characteristics of a nonlinear optical crystal.

The second object of this invention is to provide a laser light source for generating a coherent beam in the yellow range that has a narrow linewidth and excellent directivity and is energy-efficient.

From the viewpoint of environmental protection as well as health and safety, it is strongly desired to establish ultralow volume analytical techniques of environmental gases, such as $NO_x$, $SO_x$, and ammonia system, absorption peaks of water, many organic gases, and residual pesticides. As the ultralow-volume analytical techniques, a quantitative analysis in which a gas to be measured (measured gas) is adsorbed in a specific substance and an electrochemical technique is performed, and an optical method for measuring optical absorption property intrinsic to a measured substance are common. Among these, the optical method has features that real-time measurement is possible and a widespread area through which measuring light passes can be observed.

Absorption peaks of a measured substance result form vibration modes of an interatomic bonding, and exist mainly in the mid-infrared region of 2-20 μm. However, in wavelength band 112 in the mid-infrared region shown in FIG. 1, a laser capable of continuous oscillation at room temperature has not yet been put to practical use, but only research and development of the quantum cascade laser is being advanced. Industrially, although the need for mid-infrared light is high, a fact that there is no practical laser light source becomes a large obstruction to applications.

Since there is no practicable light source in the mid-infrared region, when performing microanalysis of various gases etc. using existing semiconductor lasers (0.8-2 μm) for communications, absorption at the second overtone of the fundamental absorption wavelength (=½ of the fundamental absorption wavelength) and at the third overtone. (=⅓ of the fundamental absorption wavelength) will be used. As far as the second overtone is concerned, required sensitivity may be obtained. However, measurement at a high-order absorption peak of the third or higher overtone comes with a limit in detection, because the amount of absorption itself is small. Therefore, this method will bring decrease in sensitivity by about three orders of magnitude as compared to the measurement at the original fundamental absorption wavelength.

Therefore, in order to obtain high detection sensitivity in analyzing environmental gases, gases involving risk, etc., it is indispensable to develop a mid-infrared laser light source. In recent years, it was reported that mid-infrared light was generated in the vicinity of the 3-μm wavelength, and an operation as a gas sensor was verified (for example, see Non-patent document 6). A light source used in a gas sensor generates mid-infrared light by difference frequency generation using a lithium niobium oxide ($LiNbO_3$) wavelength converter device that has a periodically poled structure.

However, the wavelength converter device having the periodically poled structure generates only mid-infrared light of a single fixed wavelength. Then, in order to make the wavelength variable so that different kinds of gases can be detected together, several methods are known as follows. (1) Several periods are provided in a single wavelength converter device (for example, see Non-patent document 7). (2) Period is changed by means of a structure called Fanout Grating (see the aforesaid Non-patent document 6). (3) Effective period is changed by making an excitation beam incident on the device slantingly (for example, see Non-patent document 8)

Although these methods can sweep a wavelength in a wide range, since the element with various periods had to be bundled, there was a problem that many operation processes were needed. Moreover, the technique of making an excitation beam incident on an element slantingly comes with a problem that it is difficult to create a waveguide structure in the device to attain high efficiency.

The third object of this invention is to provide a laser light source capable of tuning a laser beam in the mid-infrared region between 2-μm and 3-μm wavelength.

In recent years, environmental problem is coming to the fore greatly, and especially, attention centers on influences of dioxin on human body. In an incinerator that is one of origins of dioxin, generation of dioxin can be suppressed by controlling the combustion state of the furnace. For monitoring the combustion state, thermometers, CO concentration meters, and oximeters are needed.

As one technique to detect gas concentrations, there is known a method in which measured gases are irradiated with a laser beam and their absorption properties are observed. Since each gas has intrinsic absorption lines, the gas concentration can be detected by scanning a laser beam having a wavelength near the absorption line and observing an absorption spectrum. Points required for the laser beam at this occasion include monochromaticity, i.e., being a single-mode laser beam, delivering an output of a few mW to a few tens mW suited to gas detection, capability of stable wavelength scanning, long life, etc.

A laser beam used in the oximeter is in wavelength band 113 including a plurality of oxygen absorption lines existing at wavelengths of 759 nm to 768 nm, so gallium arsenide semiconductor lasers are being used (for example, see Patent document 1). A gallium arsenide semiconductor laser is manufactured by growing semiconductor crystals whose lattice constants almost agree with the lattice constant of gallium arsenide.

Semiconductor lasers are divided into the edge emitting type laser whose waveguide is manufactured in parallel to a substrate and the surface emission-type laser that emits light perpendicular to a substrate. Regarding gallium-arsenide edge emitting type lasers, relatively high-power single-mode lasers have been developed, but do not have structures to control their oscillation wavelengths. Consequently, the oscillation wavelength of the gallium-arsenide edge emitting type laser is determined at a point at which a gain peak of the active layer and a resonant mode of the resonator coincide. Therefore, the laser easily jumps among longitudinal modes at the time of wavelength scanning, and stable wavelength scanning is hard to perform.

As structures for controlling an oscillation wavelength, the distribution feedback (DFB) type, the distribution Bragg-reflection (DBR) type, etc. are well known. For these structures, it is necessary to manufacture semiconductor crystal whose refractive index is varied periodically in a direction parallel to the substrate, namely, whose composition is varied, in the semiconductor crystals. A manufacture method is that the surface of the semiconductor crystal is etched to a periodical structure, such as a corrugated shape, and thereon a semiconductor crystal of a different composition is grown. If the laser is intended to oscillate at the 763-nm wavelength in order to detect the oxygen concentration, it is necessary to suppress absorption at the wavelength and crystals of high aluminum concentrations must be used. However, if the aluminum concentration is high, there is a problem that the crystal is likely to be oxidized when manufacturing the periodic structure.

The surface emission-type laser is a kind of the DBR laser. In the surface emission-type laser, since a direction of emission is perpendicular to the substrate, the laser needs a DBR structure having a refractive index distribution in the perpendicular direction to the substrate. That is, it is only necessary to grow semiconductor crystals each of which is a layer parallel to the substrate and has a different composition so as to form a periodically stacked layers of crystals. Sine the manufacture can be completed with one round of semiconductor crystal growth, the manufacture is easy. However, since light passes through the active layer in a vertical direction in the surface emission-type laser, large gain cannot be obtained. In order to obtain sufficient output, a method for increasing the area of emission is conceivable. However, if the area of emission is increased, the laser will oscillate in a plurality of transverse modes, departing from a single-mode operation. If emission intensity of an order of mW necessary for detection of oxygen concentration is intended to be obtained while keeping a single-mode operation with a limited area of emission, current necessary for emission will concentrate in a minute area to increase the current density. For this reason, there is a problem that a life of the surface emission-type laser becomes as short as a few months.

The fourth object of this invention is to provide a laser light source that is high-power and long-life at wavelengths of 759 nm to 768 nm that are the oxygen absorption lines.

[Patent document 1] Japanese Patent Application Laid-open No. 6-194343(1994)

[Patent document 2] U.S. Pat. No. 5,036,220

[Patent document 3] Japanese Patent Laid-open No. 4-507299(1992)

[Non-patent document 1] K. Kubo and K. Katori, "Spin and Polarization," BAIFUKAN, p. 21-24 (Oct. 31, 1994)

[Non-patent document 2] Harold J. Metcalf and Peter van der Straten, "Laser Cooling and Trapping," Springer, pp. 274 (1999)

[Non-patent document 3] G. Patterson et al., J. Cell Sci., No. 114, pp. 837-838 (2001)

[Non-patent document 4] A. F. Fradkov et al., Biochem. J., No. 368, pp. 17-21 (2002)

[Non-patent document 5] D. M. Chudakov et al., Nat. Biotechnol. No. 21, pp. 191-194 (2003)

[Non-patent document 6] D. Richter, et al., Applied Optics, Vol. 39, 4444 (2000)

[Non-patent document 7] I. B. Zotova et al., Optics Letters, Vol. 28, 552 (2003)

[Non-patent document 8] C.-W. Hsu et al., Optics letters, Vol. 26, 1412 (2001)

[Non-patent document 9] A. Yariv, "Quantum Electronics," Third Ed., pp. 392-398 (1988)

[Non-patent document 10] http// laserfocusworld.365media, comilaserfocusworld/search Resultasp?cat=48903/&d=453&st=1

[Non-patent document 11] R. M. Schotland, Proc. third Symp. on Remote Sensing of Environment, 215 (1964)

[Non-patent document 12] IEEE Photonics Technology Letters, Vol. 11, pp. 653-655 (1999)

[Non-patent document 13] Proceedings of the 15th Annual Meeting of Institute of Electrical and Electronic Engineers, Lasers and Electro-Optics Society, 2002 (IEOS2002), Vol. 1, pp. 79-80 (2002)

DISCLOSURE OF THE INVENTION

The present invention provides a compact laser light source that allows a user to design its wavelength freely in a wavelength band in which the semiconductor lasers have not been put to practical use by combining an efficient nonlinear optical crystal and high-power semiconductor lasers for optical communication.

In order to achieve the first object, this invention is a laser light source that comprises: a first laser for generating a laser beam of a wavelength $\lambda_1$; a second laser for generating a laser beam of a wavelength $\lambda_2$; and a nonlinear optical crystal that uses laser beams of wavelengths $\lambda_2$, $\lambda_1$ as inputs and delivers a coherent beam of a wavelength $\lambda_3$ of a sum frequency that satisfies a relationship of $1/\lambda_1 + 1/\lambda_2 = 1/\lambda_3$; wherein the wavelength $\lambda_3$ of the sum frequency is a wavelength of 589.3±2 nm corresponding to the sodium D line.

Moreover, in order to achieve the second object, this invention is a laser light source that comprises: a first laser for generating a laser beam of a wavelength $\lambda_1$; a second laser for generating a laser beam of a wavelength $\lambda_2$; and a nonlinear optical crystal that uses laser beams of wavelengths $\lambda_2$, $\lambda_1$ as inputs and delivers a coherent beam of a wavelength $\lambda_3$ of a sum frequency that satisfies a relationship of $1/\lambda_1 + 1/\lambda_2 = 1/\lambda_3$; wherein the wavelength $\lambda_1$ is 940±10 nm, the wavelength $\lambda_2$ is 1320±20 nm, and the wavelength $\lambda_3$ of the sum frequency is 546.1±5.0 nm that corresponds to a yellow range.

Setting the wavelength $\lambda_1$ to 980±10 nm and the wavelength $\lambda_2$ to 1320±20 nm, the wavelength $\lambda_3$ of the sum frequency becomes 560.0±5.0 nm that corresponds to the yellow range. Alternately, setting the wavelength $\lambda_1$ to 1064±10 nm and the wavelength $\lambda_2$ to 1320±20 nm, the wavelength $\lambda_3$ of the sum frequency becomes 585.0±5.0 nm that corresponds to the yellow range. Further alternatively, setting the wavelength $\lambda_1$ to 940±10 nm and the wavelength $\lambda_2$ to 1550±30 nm, the wavelength $\lambda_3$ of the sum frequency becomes 585.0±5.0 nm that corresponds to the yellow range.

Furthermore, in order to achieve the third object, this invention is a laser light source that comprises: a first laser for generating a laser beam of a wavelength $\lambda_1$; a second laser for generating a laser beam of a wavelength $\lambda_2$; and a nonlinear optical crystal that uses the laser beams of wavelengths $\lambda_2$, $\lambda_1$ as inputs and delivers a coherent beam of a wavelength $\lambda_3$ of a difference frequency that satisfies a relationship of $1/\lambda_1 - 1/\lambda_2 = 1/\lambda_3$; wherein the at wavelength $\lambda_1$ is in a range of 0.9-1.0 μm and the nonlinear optical crystal has a periodically poled structure of a single period that is configured so that the wavelength $\lambda_3$ varies between 3.1 μm and 2.0 μm when the wavelength λ2 varies between 1.3 μm and 1.8 μm.

Even furthermore, in order to achieve the fourth object, the laser light source comprises: a distributed feedback semiconductor laser for oscillating a laser beam having a wavelength twice the wavelength of a single absorption line selected from among oxygen absorption lines that exist at wavelengths of 759 nm to 768 nm; an optical waveguide having a second-order nonlinear optical effect; a polarization maintaining fiber that connects an output of the distributed feedback semiconductor laser and one end of the optical waveguide.

BEST MODE FOR CARRYING OUT THE INVENTION

Figure 1:
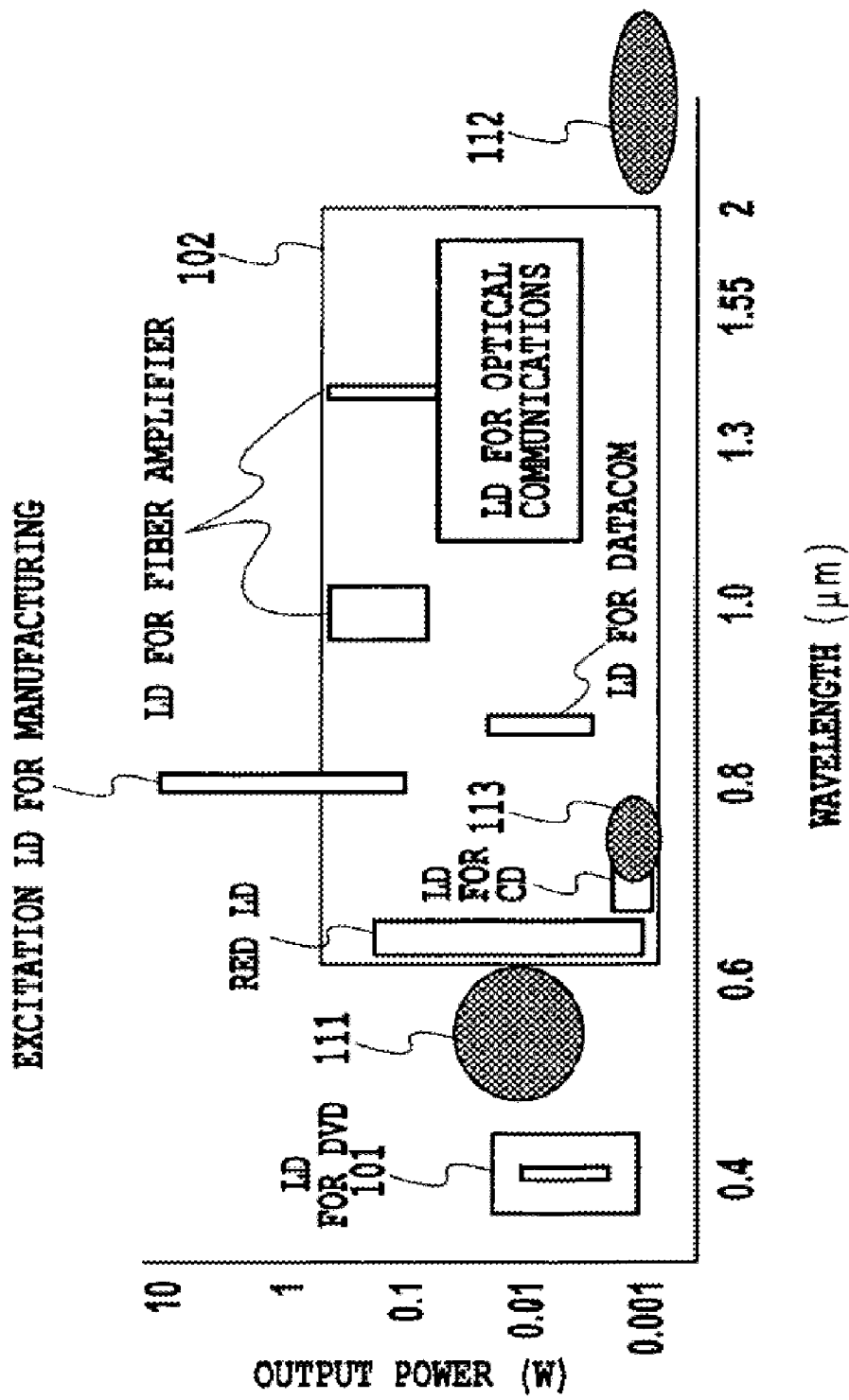
FIG. 1 is a diagram showing a relationship between laser wavelength band and output power.
Figure 2:
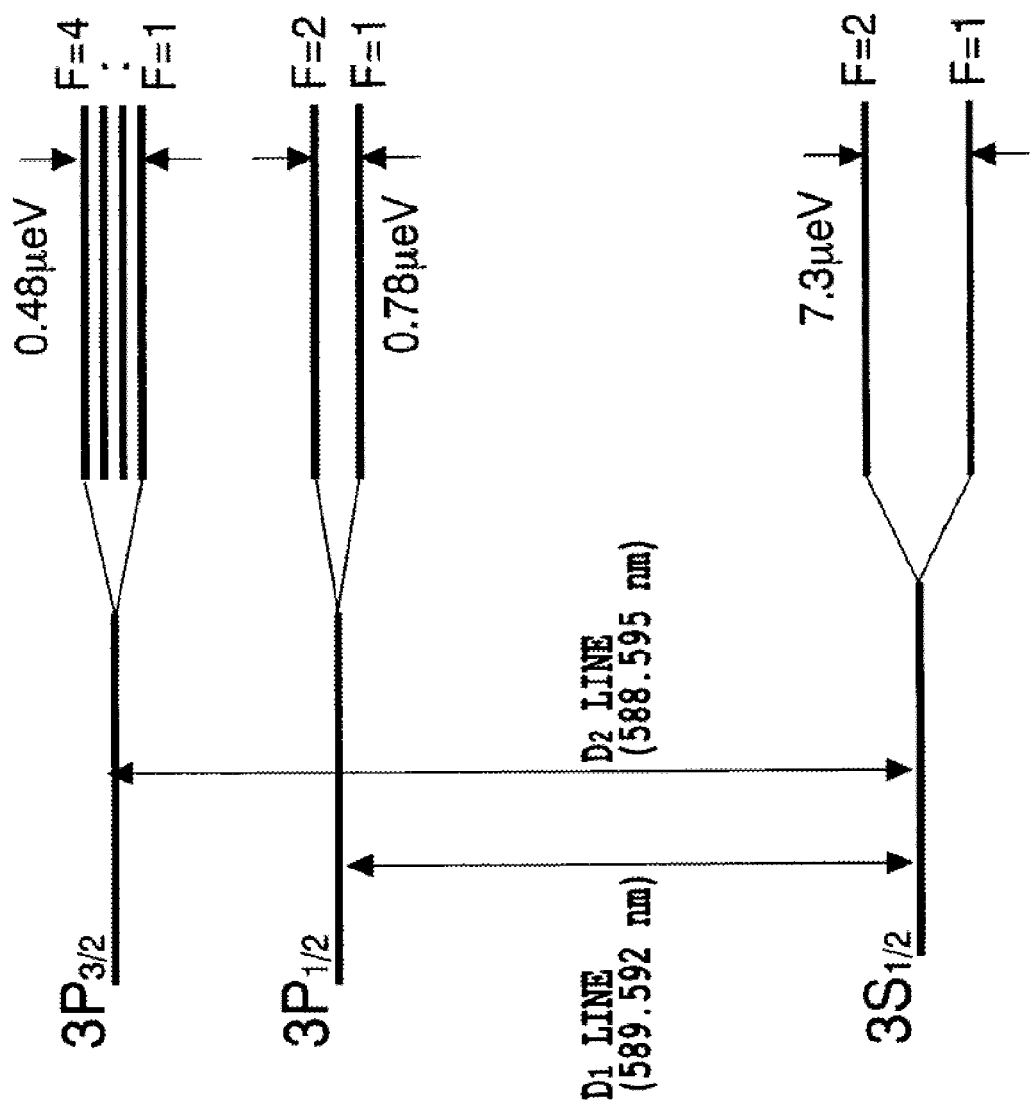
FIG. 2 is a diagram showing the energy levels of a sodium atom.
Figure 3:
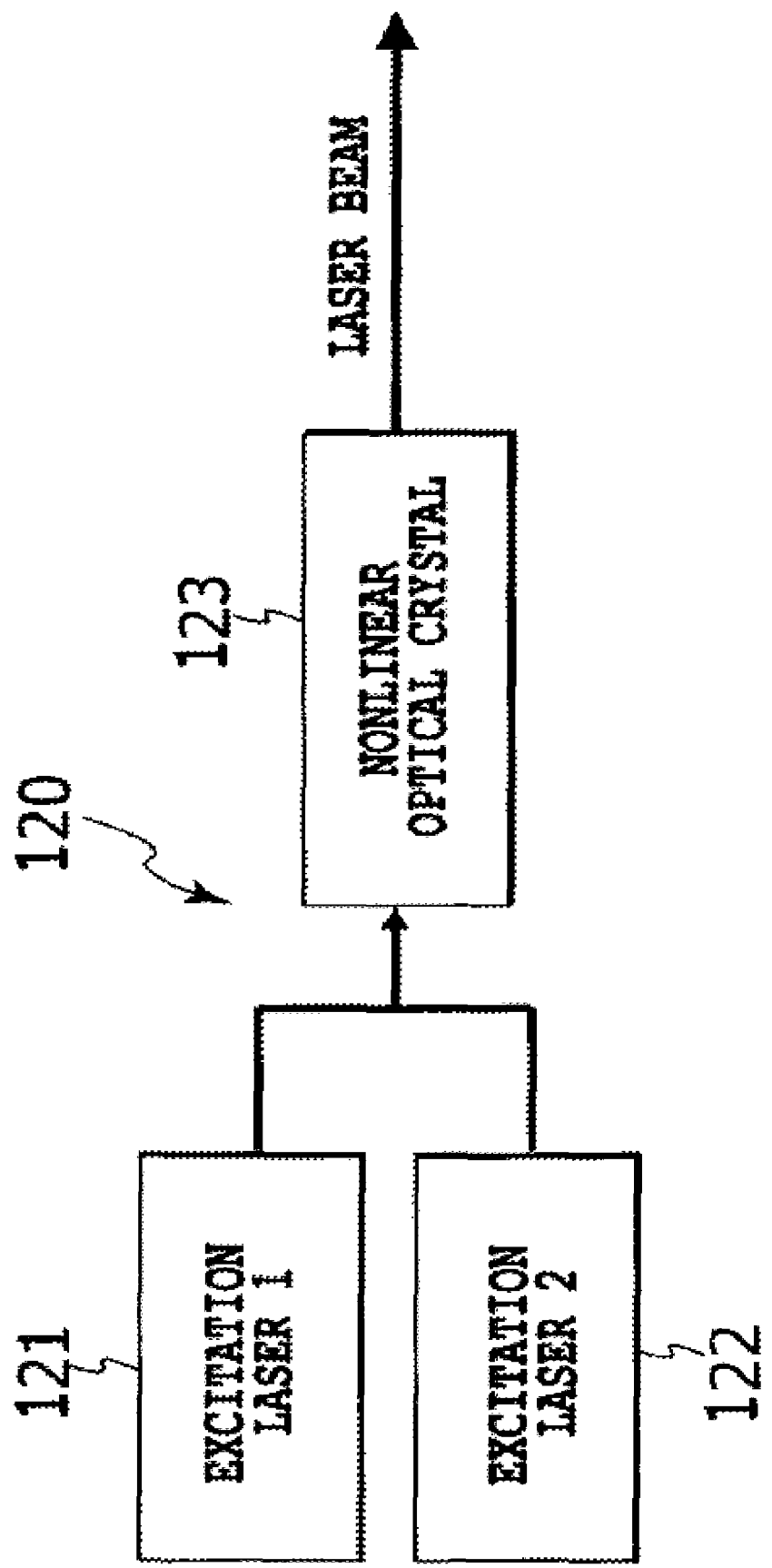
FIG. 3 is a block diagram of a laser light source according to one embodiment of this invention.

Hereafter, embodiments of this invention will be described in detail referring to drawings. In these embodiments, an efficient nonlinear optical crystal and high-power semiconductor lasers for optical communication are combined. FIG. 3 shows a laser light source according to one embodiment of this invention. A laser light source 120 consists of two excitation lasers 121,122 for exciting a nonlinear optical crystal, and a nonlinear optical crystal 123 for generating sum frequency light or difference frequency light. Incidentally, second overtone generation of an output beam from one excitation laser inputted into a nonlinear optical crystal may be used in some wavelengths.

First Embodiment

In sum frequency generation using a nonlinear crystal, the wavelength $\lambda_3$ of the sum frequency light is expressed by the following formula, using the wavelengths of the two excitation beams represented by $\lambda_1$ and $\lambda_2$.

$$1/\lambda_3=1/\lambda_1+1/\lambda_2 \qquad (1)$$

In order to generate the sum frequency light equivalent to the sodium D1 line and D2 line, it is necessary to select $\lambda_1$ and $\lambda_2$ that give $\lambda_3=589.592$ nm or 588.995 nm in the formula (1) and then combine the excitation lasers 121,122 of the two wavelengths with the nonlinear optical crystal 123.

Moreover, to increase the generation efficiency of the sum frequency light, the following formula must be satisfied among propagation constants $k_i=2\pi n_i/\lambda_i$ (i=1, 2, 3) of the two incident beams in the nonlinear optical crystal ($\lambda_1$, $\lambda_2$), and of the sum frequency light ($\lambda_3$)

$$k_3=k_1+k_2, \qquad (2)$$

where $n_i$ is a refractive index of the nonlinear crystal at $\lambda_i$. However, since the optical medium has a dispersion characteristic, the formula (2) is satisfied only under specific conditions. To be concrete, there is a method in which a polarization direction of any one of the incident beams and the sum frequency light is changed and both the refractive index of ordinary ray and the refractive index of extraordinary ray are used (for example, see Non-patent document 9). Alternately, a method in which a periodically poled structure is formed in a nonlinear optical crystal, and enhancement of the conversion efficiency is achieved by quasi-phase matching is being used (see Patent document 2 and corresponding Patent document 3).

Since the generation intensity of the sum frequency light is proportional to a product of intensities of the two excitation beams, the selection of the two excitation beams is done in such a way that a combination of wavelengths satisfies the formula (1) and the lasers have much higher intensities. Among the wavelength bands of existing semiconductor lasers (for example, they are summarized in Non-patent document 10), the wavelength bands in which high power has been made available are (1) 940-nm band, (2) 980-nm band, (3) 1060-nm band, and (5) 1480-nm band. In addition, semiconductor lasers of a 100-mW class are being developed also in (4) 1300-nm band and (6) 1550-nm band. Especially, in the ranges of (4), (5), and (6), DFB (Distributed FeedBack) lasers are being developed, and single longitudinal mode oscillation and wavelength stabilization have been realized. Although even in the 800-880 nm range, high-power semiconductor lasers have been developed, if a semiconductor laser in this range is used as an excitation laser 1, the wavelength of an excitation laser 2 will be set to 1780 nm or more. Since it is difficult to realize high-power and high-reliability semiconductor lasers in such a long wavelength band, this combination is excluded.

Figure 4:
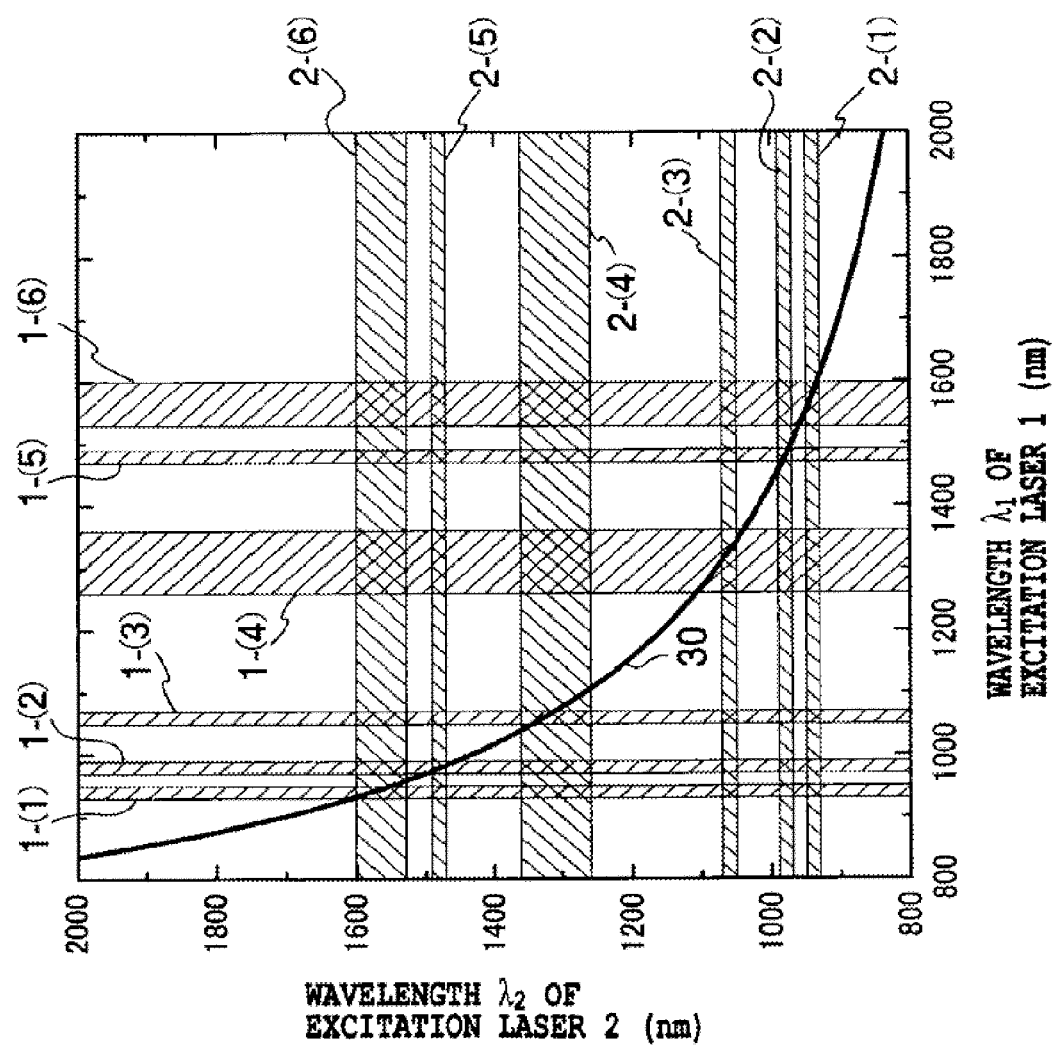
FIG. 4 is a diagram showing a relationship of wavelength between an excitation laser 1 and an excitation laser 2 for obtaining a wavelength of the sodium D line by sum frequency generation.

FIG. 4 shows a relationship of wavelength between the excitation laser 1 and the excitation laser 2 for obtaining a wavelength of the sodium D line wavelength by sum frequency generation. The figure show a relationship for obtaining the sum frequency light, using the wavelengths of the excitation lasers 1 and 2 represented by $\lambda_1$ and $\lambda_2$, respectively. Wavelength bands of the excitation laser 1 for the above (1) through (6) are designated by 1-(1), 1-(2), 1-(3), 1-(4), 1-(5), and 1-(6), respectively, and shown by hatching. In addition, wavelength bands of the excitation laser 2 of the above (1) through (6) are designated as 2-(1), 2-(2), 2-(3), 2-(4), 2-(5), and 2-(6), respectively, and shown by hatching. FIG. 4 indicates that, when using a combination of the excitation laser 1 and the excitation laser 2 such that any one of 1-(1) through 1-(6) and any one of 2-(1) through 2-(6) intersect on a curve 30, high-efficiency sum frequency generation becomes possible.

The ranges of (1) through (6) are set as follows:

(1) 940±10 nm (2) 980±10 nm (3) 1060±10 nm (4) 1280 nm to 1350 nm (5) 1480±10 nm (6) 1530 nm to 1600 nm

Incidentally, (5) is the O band and (6) is the C band in optical communications. These two wavelength bands are ranges that are being used most frequently and in which optical parts, such as high-power and high-reliability semiconductor lasers, are easily obtained.

For the combination of any one of 1-(1) through 1-(6) and any one of 2-(1) through 2-(6) that intersect on the curve 30, it is necessary to consider that the same sum frequency wavelength can be obtained if the wavelengths of the excitation laser 1 and the excitation laser 2 are exchanged. This consideration leads to a conclusion that combinations of (1) and (6), (2) and (5), and (3) and (4) make intersection on the curve 30 and the use of one of these combinations enables the wavelength of the sodium D line to be generated efficiently.

Generally, in terms of modes of the laser, there are a single-mode oscillation and a multimode oscillation. The characteristics of the sum frequency generation light are determined by the characteristics of the two excitation semiconductor lasers. In order to perform a single mode oscillation of the sum frequency generation light, the two semiconductor lasers for excitation need to be oscillated in a single mode. For this purpose, the use of a semiconductor laser having a DFB structure or a laser that uses a fiber Bragg grating in its resonator structure becomes necessary. On the other hand, in the case of the multimode oscillation, it can be achieved by using a Fabry-Perot type semiconductor laser or a semiconductor laser such that a fiber grating having a reflection spectrum of a full width of half maximum of about 0.1-0.5 nm is applied to its resonator structure.

For a nonlinear optical crystal, any crystal that has a large nonlinear optical constant and is transparent at the wavelengths of the two lasers used for excitation and at the sodium D line wavelength can be used. As a concrete example, lithium niobium oxide ($LiNbO_3$, LN), lithium tantalum oxide ($LiTaO_3$, LT), etc. can be enumerated. Moreover, in order that these nonlinear optical crystals may perform sum frequency generation efficiently, it is preferable to have the periodically poled structure and a waveguide structure.

The periodically poled structure is a grating structure in which a direction of polarization is reversed by 180 degrees with a period $\Lambda$ to a propagation direction of light. With this structure, a quasi-phase matching condition such that the amount of phase mismatching becomes zero is satisfied. Representing refractive indices of a nonlinear optical crystal at wavelengths $\lambda_1$, $\lambda_2$, and $\lambda_3$ as $n_1$, $n_2$, and $n_3$, respectively, if the structure is made to be the periodically poled structure that satisfies $$2\pi n_3/\lambda_3 = 2\pi n_1/\lambda_1 + 2\pi n_2/\lambda_2 + 2\pi n_2/\Lambda, \quad (3)$$

The generation efficiency of the sum frequency light can be maximized.

In addition, since the formation of a waveguide in a nonlinear optical crystal enables the incident beams from the excitation lasers to be confined efficiently, the sum frequency light can be generated efficiently. The periodically poled structure can be realized by an electric field application method, and the waveguide structure can be realized by the proton exchange method, a dry etching method, a machining method using a dicing saw, or the like. The method for manufacturing a waveguide will be described later as a fifth embodiment.

Moreover, the generation of the sum frequency light needs coupling of the two semiconductor laser beams and coupling of them to an LN waveguide. These techniques have been established as optical communication device technologies, featuring that there is not a large obstacle in implementing the coupling.

For example, the linewidth of the existing semiconductor DFB laser is 1 MHz, and the linewidth of the external mirror resonator-type semiconductor laser using a fiber Bragg grating is about 100 kHz. The linewidth of the sum frequency light when these lasers are used as excitation lasers is a few MHz or less, which is estimated by convolution integral of the two linewidths of the excitation beams. In the case where the refractive index at the sodium D line (wavelength: 589.3 nm, frequency: approximately 500 THz) by interferometry, its measurement accuracy is given by a ratio of the linewidth to the frequency of the laser beam used. Assuming that the linewidth is 5 MHz, the measurement accuracy is $10^{-8}$. Therefore, according to this embodiment, it becomes possible to improve the accuracy of the refractive index measurement by about two orders of magnitude compared to the present state.

As explained in the foregoing, the coherent beams having wavelengths of the sodium D1 line and D2 line can be generated efficiently in a highly stable manner by selection of existing laser devices together with improvement of characteristics of a nonlinear optical crystal, which makes it possible to minimize a laser light source and to enhance the accuracy of the refractive index measurement.

Embodiment 1-1

Figure 5:
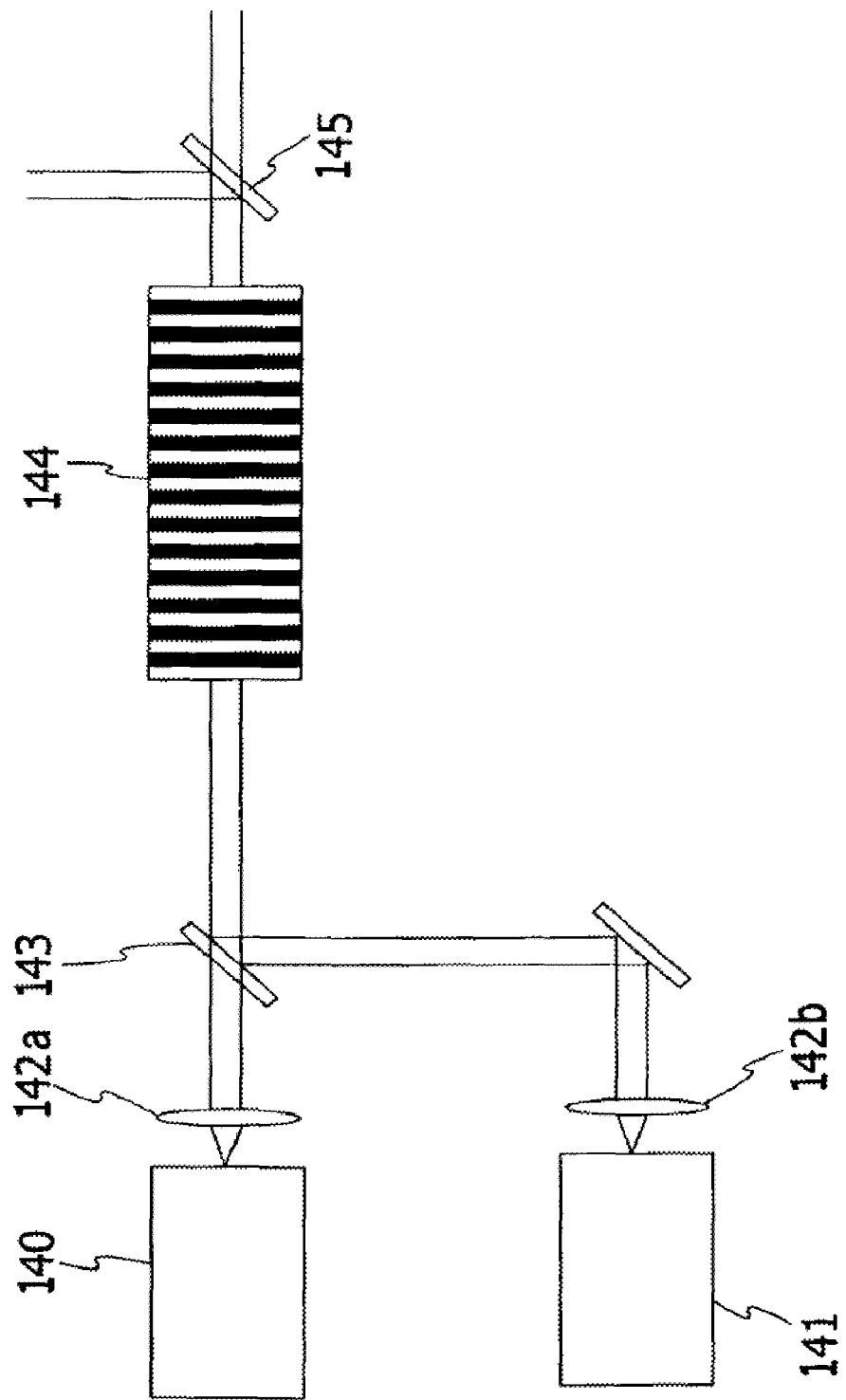
FIG. 5 is a block diagram of a laser light source of the sodium D-line wavelength according to Embodiment 1-1 of this invention.

FIG. 5 shows a laser light source of the sodium D-line wavelength according to Embodiment 1-1 of this invention. The laser light source is constructed with two excitation lasers 140, 141, an LN 144 whose polarization was reversed periodically, lenses 142a, 142b for collimating laser beams of the excitation lasers 140, 141, a multiplexer 143 for multiplexing two laser beams, and a filter 145 for separating the laser beams of the excitation lasers 140, 141 that passed through the LN 144 and the sum frequency light generated in the LN 144.

The wavelength $\lambda_1$ of the excitation laser 140 and the wavelength $\lambda_2$ of the excitation laser 141 are specified of to be of a combination that satisfies $$1/\lambda_1 + 1/\lambda_2 = 1/(589.3 \pm 2.0).$$

Moreover, $\lambda_1$ and $\lambda_2$ are in wavelength bands that satisfy any one of the following sets.

$\lambda_1 = 976 \pm 10$ nm, $\lambda_2 = 1485 \pm 20$ nm $\lambda_1 = 1064 \pm 10$ nm, $\lambda_2 = 1320 \pm 20$ nm $\lambda_1 = 940 \pm 10$ nm, $\lambda_2 = 1565 \pm 35$ nm The semiconductor laser of $\lambda_2$ may be a DFB laser.

When the excitation laser 140 is set so that a wavelength $\lambda_1=1064$ nm and the incident intensity on the LN 144 is 50 mW and the excitation laser 141 is set so that a wavelength $\lambda_2=1320$ nm and the incident intensity on the LN 144 is 70 mW, the sum frequency light whose wavelength $\lambda_3$ was 589.1 nm and output was 20 μW was obtained.

Embodiment 1-2

Figure 6:
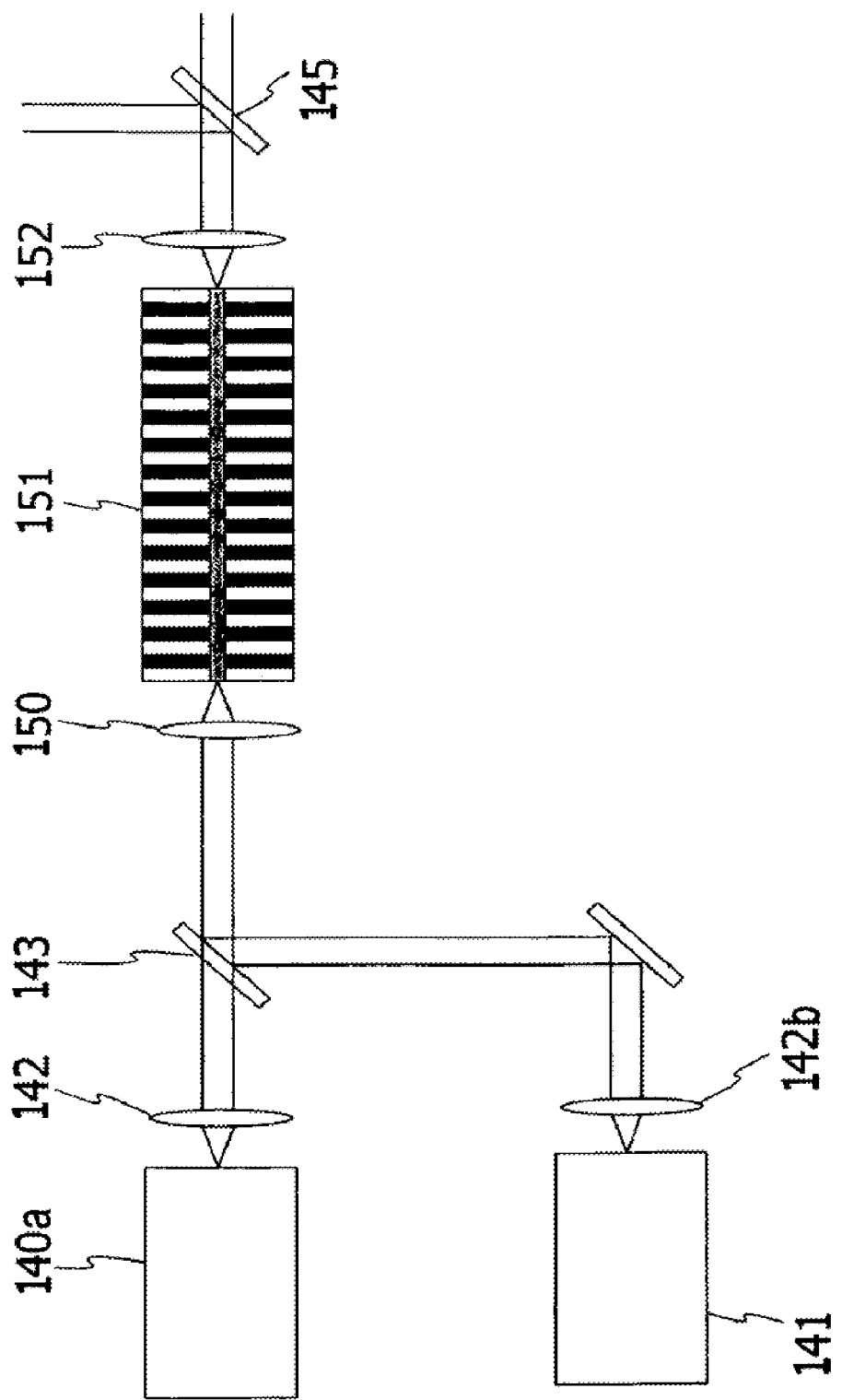
FIG. 6 is a block diagram of a laser light source of the sodium D-line wavelength according to Embodiment 1-2 of this invention.

FIG. 6 shows a laser light source of the sodium D-line wavelength according to Embodiment 1-2 of this invention. A difference from the laser light source of Embodiment 1-1 lies in a nonlinear optical crystal. For the nonlinear optical crystal, a periodically poled LN waveguide 151 such that a waveguide was formed in an LN crystal was used. Moreover, the nonlinear optical crystal has a lens 150 that couples the incident laser beam to the periodically poled LN waveguide 151 efficiently and a lens 152 that collimates the emitted beam from the periodically poled LN waveguide 151.

When the excitation laser 140 was set so that a wavelength $\lambda_1=1064$ nm and the incident intensity on the LN 144 was 50 mW and the excitation laser 141 was set so that a wavelength $\lambda_2=1320$ nm and the incident intensity on the LN 144 was 70 mW, the sum frequency light whose wavelength $\lambda_3$ was 589.1 nm and output was 10 mW was obtained.

Embodiment 1-3

To construct Embodiment 1-3, in the configurations of Embodiment 1-1 and Embodiment 1-2 (FIG. 4 and FIG. 5), the excitation laser 140 is specified to be a laser using a Nd ion whose wavelength is near 1064 nm (for example, Nd-YAG laser) and the excitation laser 141 is specified to be a semiconductor laser whose wavelength is 1300±10 nm.

Embodiment 1-4

Figure 7:
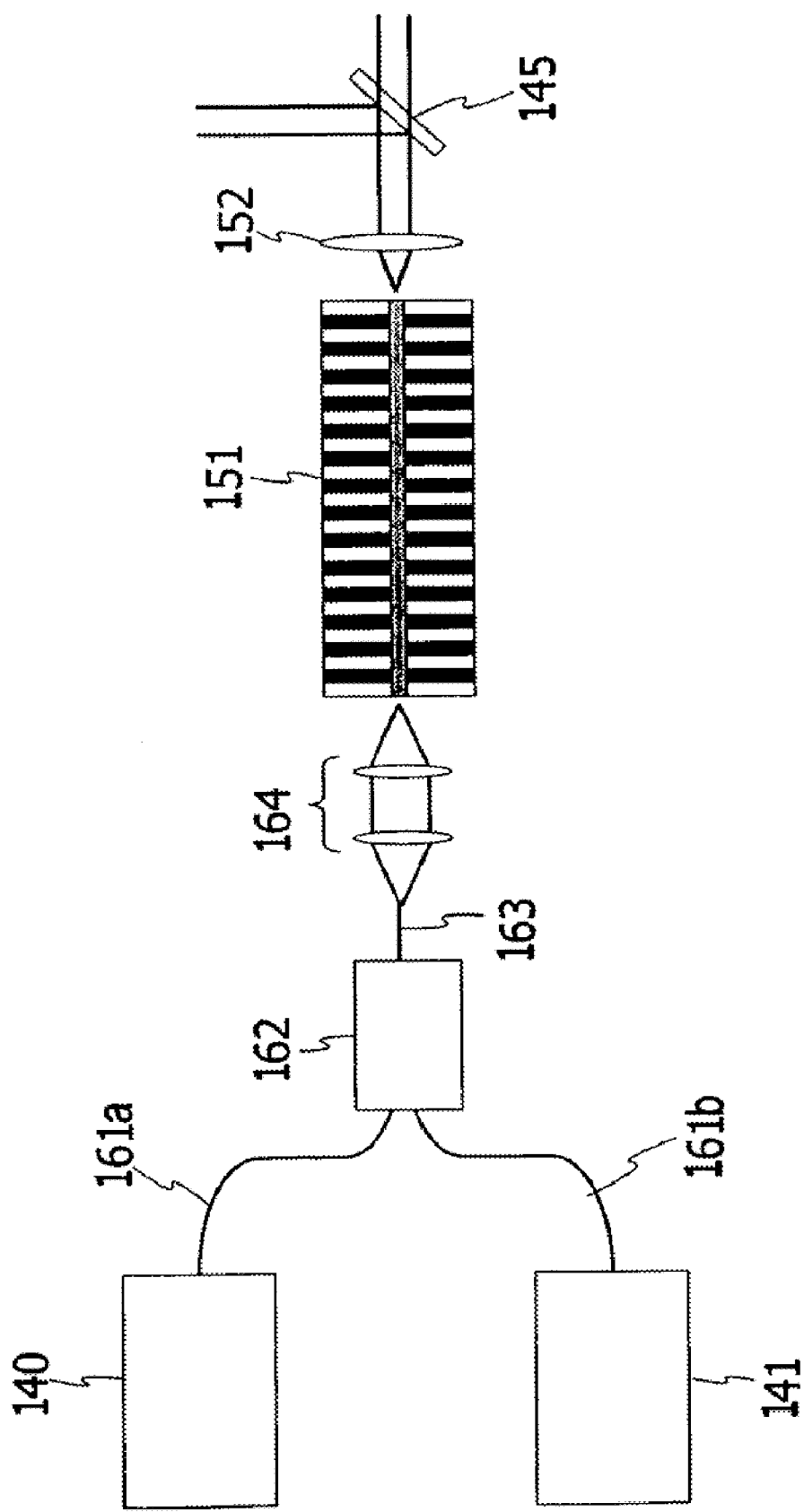
FIG. 7 is a block diagram of a laser light source of the sodium D-line wavelength according to Embodiment 1-4 of this invention.

FIG. 7 shows a laser light source of the sodium D-line wavelength according to Embodiment 1-4 of this invention. To construct Embodiment 1-4, polarization maintaining fibers (or single mode fibers) 161,163 and a multiplexer 162 are used in order to couple the two laser beams to the periodically poled LN waveguide 151 in the configuration of Embodiment 1-2. The beam emitted from the polarization maintaining fiber 163 is incident directly on a facet of the periodically poled LN waveguide 151, or is coupled thereto with a lens 164.

Embodiment 1-5

Figure 8:
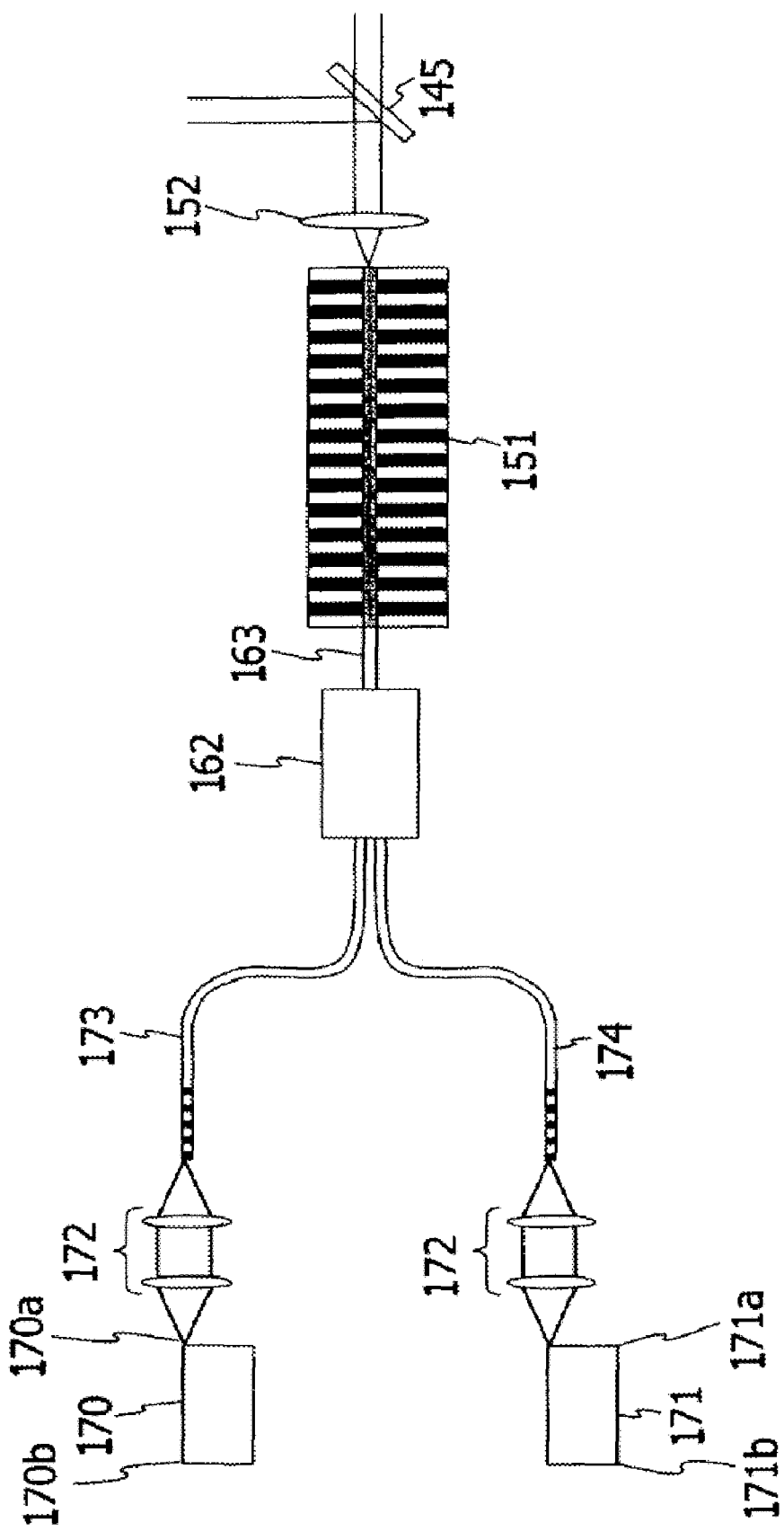
FIG. 8 is a block diagram of a laser light source of the sodium D-line wavelength according to Embodiment 1-5 of this invention.

FIG. 8 shows a laser light source of the sodium D-line wavelength according to Embodiment 1-5 of this invention. Embodiment 1-5 is an example of further application of Embodiment 1-4. In excitation lasers 170,171, AR coatings of a reflectance of 2% or less are applied on light-emitting side facets 170a, 171a and HR coatings of a reflectance of 90% or more are applied on opposite facets 170b, 171b. An output of the excitation laser 170 (171) is coupled, through a lens 172a (172b), to a polarization maintaining fiber (or single mode fiber) 173 (174) such that at its facet or at some midpoint therein a fiber Bragg grating was formed. Thus, resonators are constructed between the HR coating on the facet 170b (171b) and the fiber Bragg grating.

An oscillation wavelength of each laser is controlled by the reflection spectrum of the fiber Bragg grating. At this time, the central wavelengths of the reflection spectra of the fiber Bragg gratings are specified to be any one of the following pairs.

976±10 nm, 1485±20 nm
1064±10 nm, 1320±20 nm
940±10 nm, 1565±35 nm

The linewidths (full widths at half maximums) of the reflection spectra are specified to be 0.3 nm or less, respectively.

Second Embodiment

The configuration of a laser light source in the yellow range according to one embodiment of this invention is as shown in FIG. 3. In order to generate the sum frequency light that corresponds to the yellow range, it is necessary to select the wavelengths $\lambda_1$, $\lambda_2$ that will generate $\lambda_3$ of 546.1 nm, 560.0 nm, or 585.0 nm in the formula (1) and combine the two excitation lasers 121, 122 of two wavelengths and the nonlinear optical crystal 123.

Figure 9:
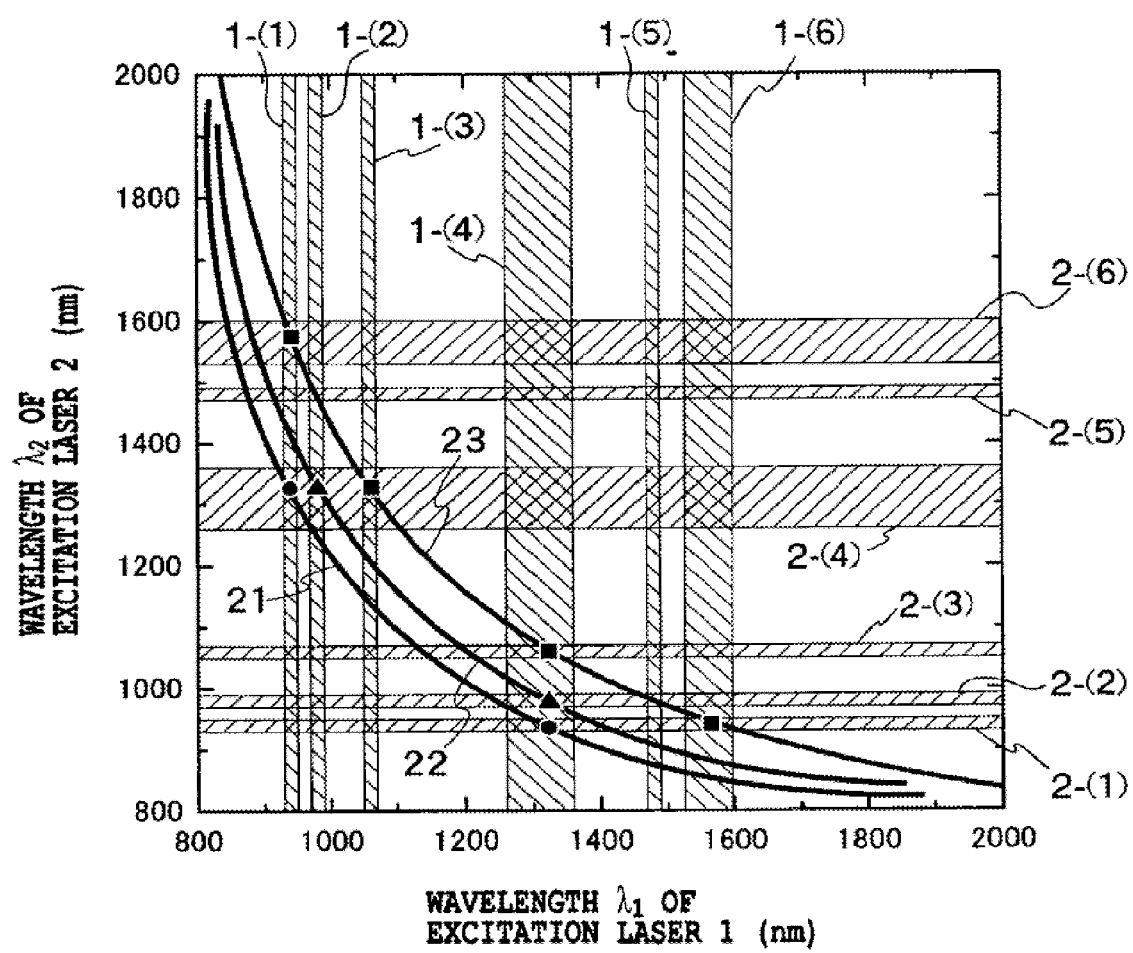
FIG. 9 is a diagram showing a relationship of wavelength between the excitation laser 1 and the excitation laser 2 for obtaining a wavelength in the yellow range by sum frequency generation.

FIG. 9 shows a relationship of wavelength between the excitation laser 1 and the excitation laser 2 to obtain a wavelength in the yellow range by sum frequency generation. Representing the wavelength of the excitation laser 1 and the wavelength of the excitation laser 2 by $\lambda_1$ and $\lambda_2$, respectively, a relationship for obtaining the sum frequency light is indicated by the curve 30. Moreover, wavelength bands of the excitation laser 1 of the above (1) through (6) are designated as 1-(1), 1-(2), 1-(3), 1-(4), 1-(5), and 1-(6), respectively, and shown by hatching. In addition, wavelength bands of the excitation laser 2 of the above (1) through (6) are designated as 2-(1), 2-(2), 2-(3), 2-(4), 2-(5), and 2-(6), respectively, and shown by hatching. Incidentally, the ranges of (1) though (6) are the same as those in FIG. 4.

FIG. 9 indicates that high-efficiency sum frequency generation becomes possible by using a combination of the excitation laser 1 and the excitation laser 2 such that any one of 1-(1) through 1-(6) and any one of 2-(1) through 2-(6) intersect on a curve 21 giving $\lambda_3=546.1$ nm, or on a curve 22 giving $\lambda_3=560.0$ nm, or on a curve 23 giving $\lambda_3=585.0$ nm.

For the combination of any one of 1-(1) through 1-(6) and any one of 2-(1) through 2-(6) that intersect on the curves 21-23, it is necessary to consider that the same sum frequency wavelength can be obtained if the wavelengths of the excitation laser 1 and the excitation laser 2 are exchanged. This consideration leads to a conclusion that when any one of combinations of (1) and (4), (2) and (4), (3) and (4), and (1) and (6) is used, a wavelength in the yellow range can be generated efficiently.

As described in the foregoing, the selection of existing laser devices, together with improvement in characteristics of a nonlinear optical crystal, enables a coherent beam in the yellow range to be generated efficiently in a highly stable manner, which makes it possible to miniaturize a laser light source and improve accuracy of refractive index measurement.

Embodiment 2-1

Figure 10:
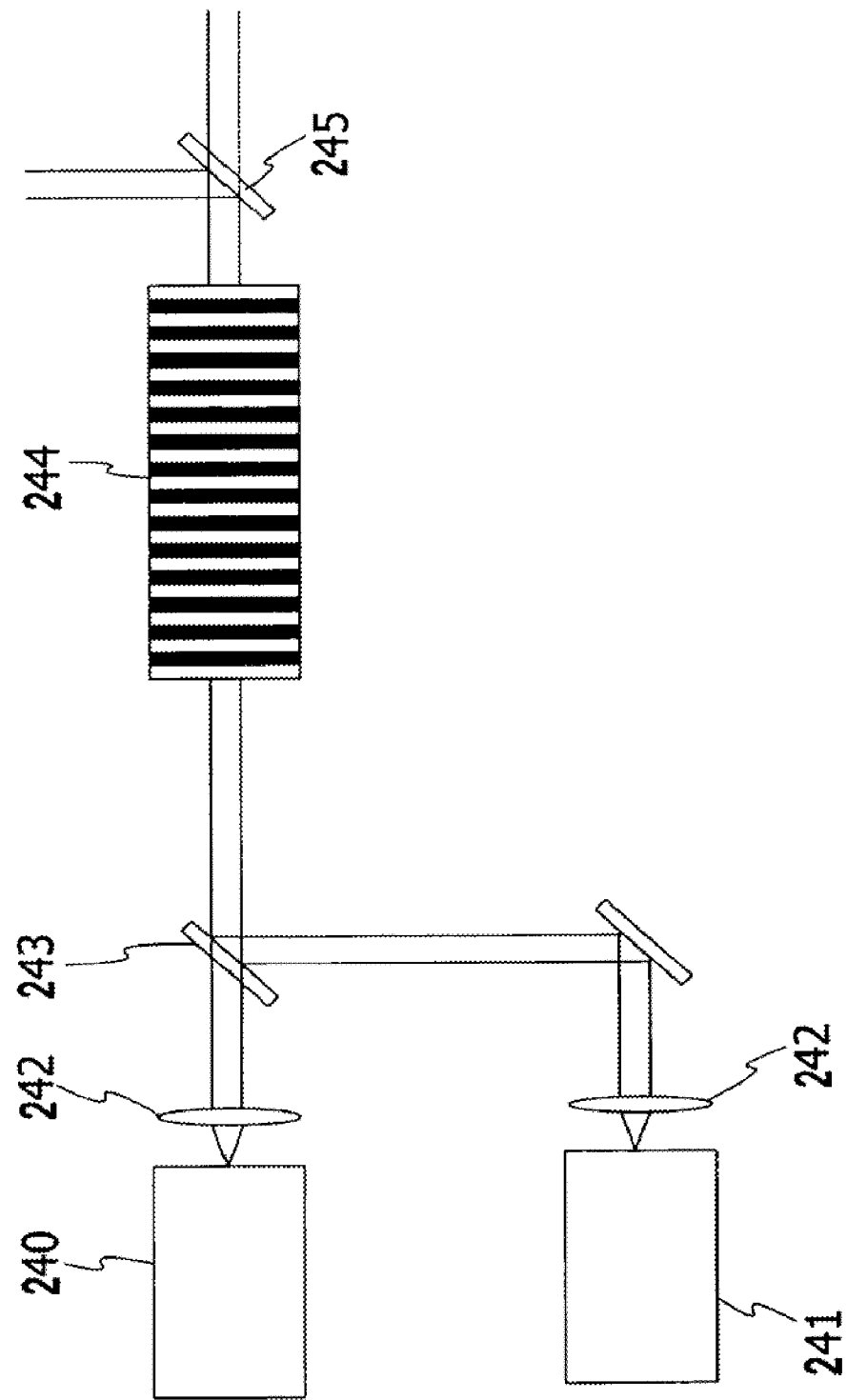
FIG. 10 is a block diagram of a laser light source in the yellow range according to Embodiment 2-1 of this invention.

FIG. 10 shows a laser light source in the yellow range according to Embodiment 2-1 of this invention. The laser light source is constructed with two excitation lasers 240, 241, an LN 244 whose polarization is reversed periodically, lenses 242a, 242b each for collimating one of the laser beams of the excitation lasers 240, 241, a multiplexer 243 for multiplexing two laser beams, and a filter 245 for separating the sum frequency light generated in the LN 244 from the laser beams of the excitation lasers 240, 241 that passed through the LN 244.

The wavelength $\lambda_1$ of the excitation laser 240 and the wavelength $\lambda_2$ of the excitation laser 241 are specified to be a pair that satisfies $$1/\lambda_1 + 1/\lambda_2 = 1/(546.1 \pm 5.0)$$

Moreover, the pair of $\lambda_1$ and $\lambda_2$ is specified to be any one of the aforesaid combinations of (1) through (4) and be in the range that satisfies $$\lambda_1 = 940 \pm 10 \text{ nm}, \lambda_2 = 1320 \pm 20 \text{ nm}$$

The semiconductor laser of $\lambda_2$ may be a DFB laser.

When the excitation laser 240 was set so that a wavelength $\lambda_1$=940 nm and the incident intensity on the LN 244 was 40 mW and the excitation laser 241 was set so that a wavelength $\lambda_{2=1320}$ nm and the incident intensity on the LN 244 was 70 mW, the sum frequency light whose wavelength $\lambda_3$ was 546.1 nm and output was 20 µW was obtained.

Embodiment 2-2

Figure 11:
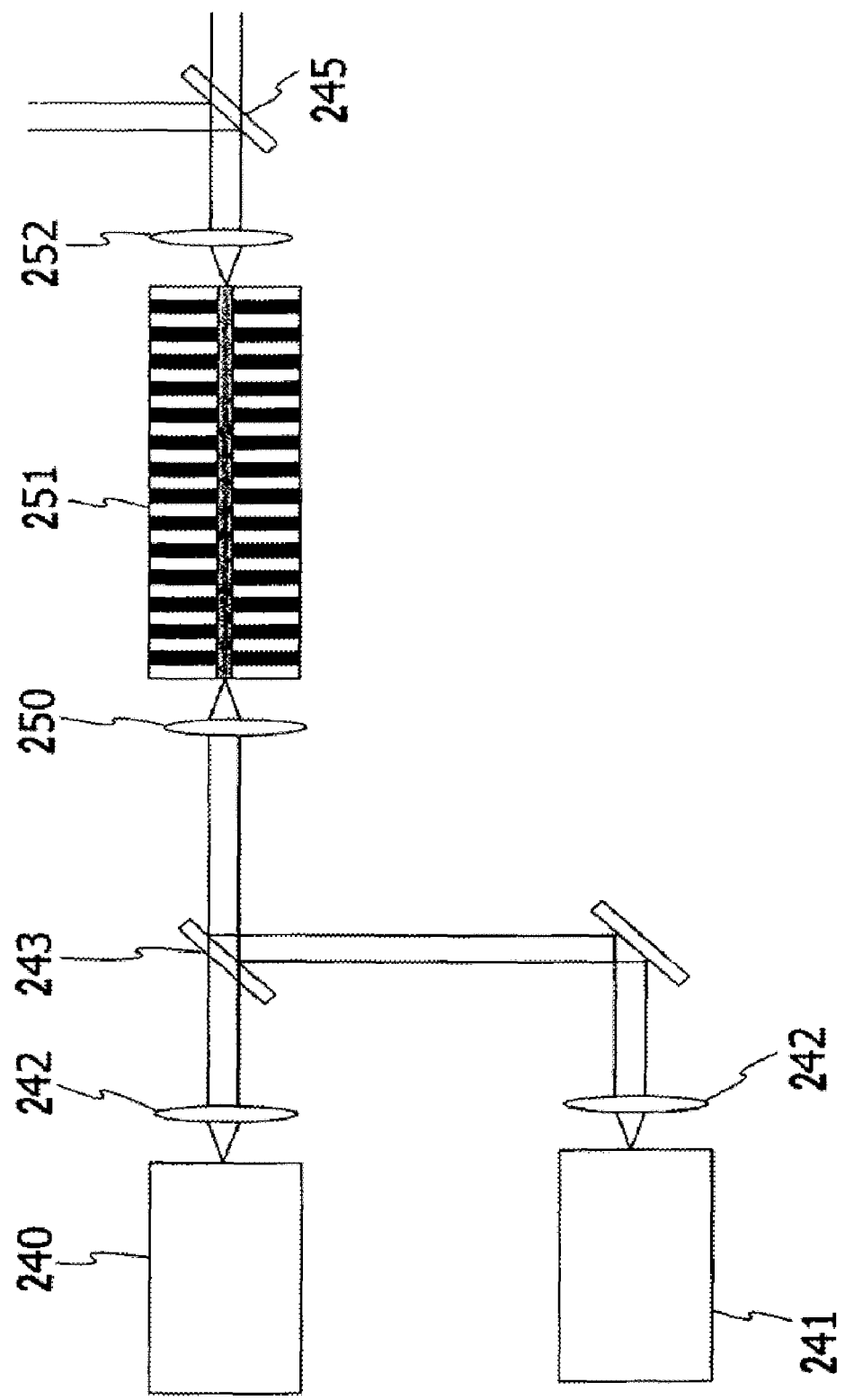
FIG. 11 is a block diagram of a laser light source in the yellow range according to Embodiment 2-2 of this invention.

FIG. 11 shows a laser light source in the yellow range according to Embodiment 2-2 of this invention. A difference from the laser light source of Embodiment 2-1 lies in a nonlinear optical crystal. Regarding the nonlinear optical crystal, a periodically poled LN waveguide 251 such that a waveguide is formed in an LN crystal is used. Moreover, the laser light source has a lens 250 for efficiently coupling the incident beams to the periodically poled LN waveguide 251 and a lens 252 for collimating the emitted beam from the periodically poled LN waveguide 251.

When the excitation laser 240 was set so that a wavelength $\lambda_1$=940 nm and the incident intensity on the LN 244 was 40 mW and the excitation laser 241 was set so that a wavelength $\lambda_2$=1320 nm and the incident intensity on the LN 244 was 70 mW, the sum frequency light whose wavelength $\lambda_3$ was 546.1 nm and output was 10 mW was obtained.

Embodiment 2-3

To construct Embodiment 2-3, the excitation laser 240 is specified to be a laser using a Nd ion whose wavelength is near 1064 nm (for example, Nd-YAG laser) and the excitation laser 241 is specified to be a semiconductor laser whose wavelength is 1320±20 nm in the configurations of Embodiment 2-1 and Embodiment 2-2 (FIG. 10 and FIG. 11). Therefore, this embodiment uses the aforesaid combination of (3) and (4), and the sum frequency light of a wavelength $\lambda_3$=585.0 nm in the yellow range can be obtained.

Embodiment 2-4

Figure 12:
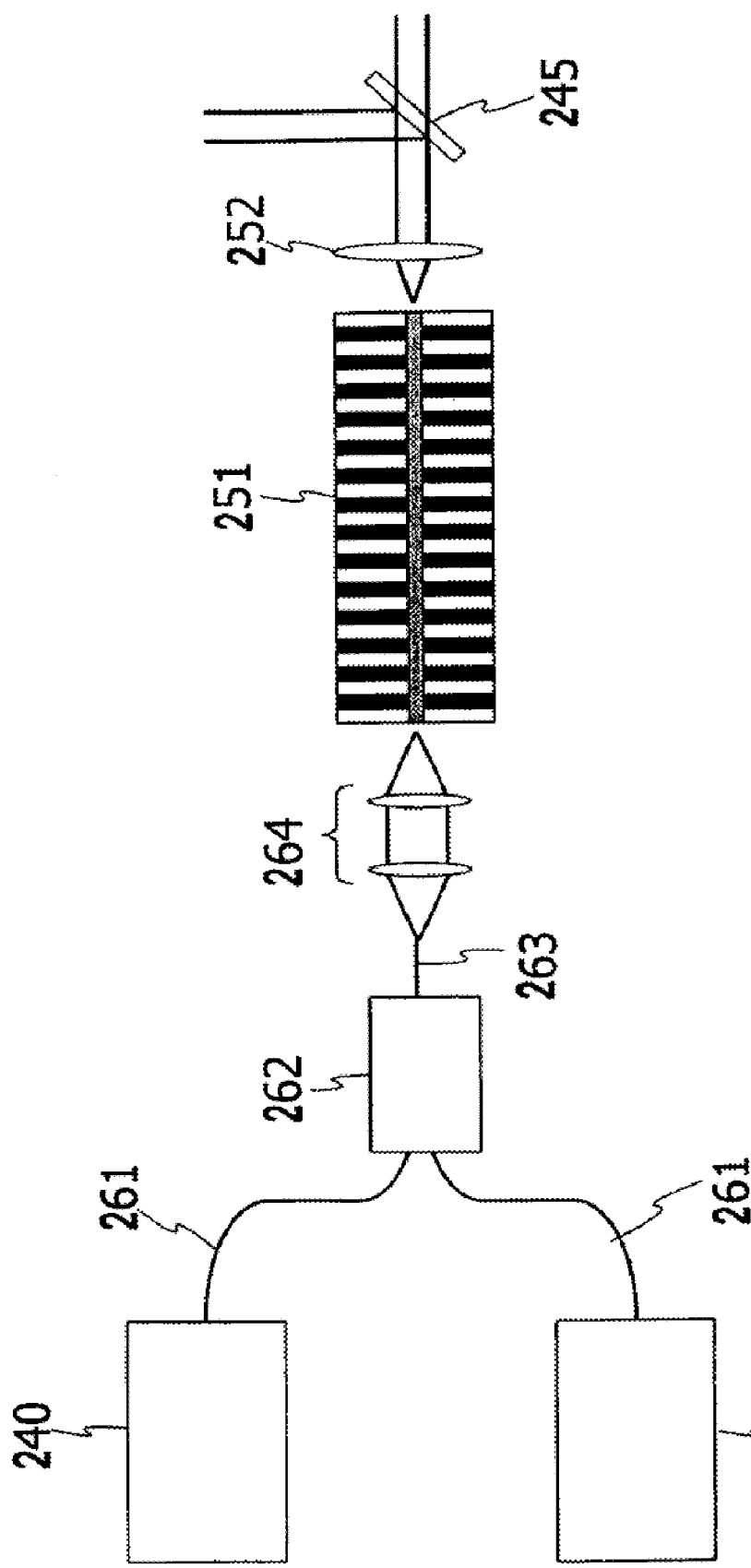
FIG. 12 is a block diagram of a laser light source in the yellow range according to Embodiment 2-4 of this invention.

FIG. 12 shows a laser light source in the yellow range according to Embodiment 2-4 of this invention. In the configuration of Embodiment 2-2, polarization maintaining fibers (or single mode fibers) 261,263 and a multiplexer 262 were used in order to couple two laser beams to the periodically poled LN waveguide 251. The beam emitted from the polarization maintaining fiber 263 is incident directly on the facet of the periodically poled LN waveguide 251, or is coupled thereto with a lens 264.

Embodiment 2-5

Figure 13:
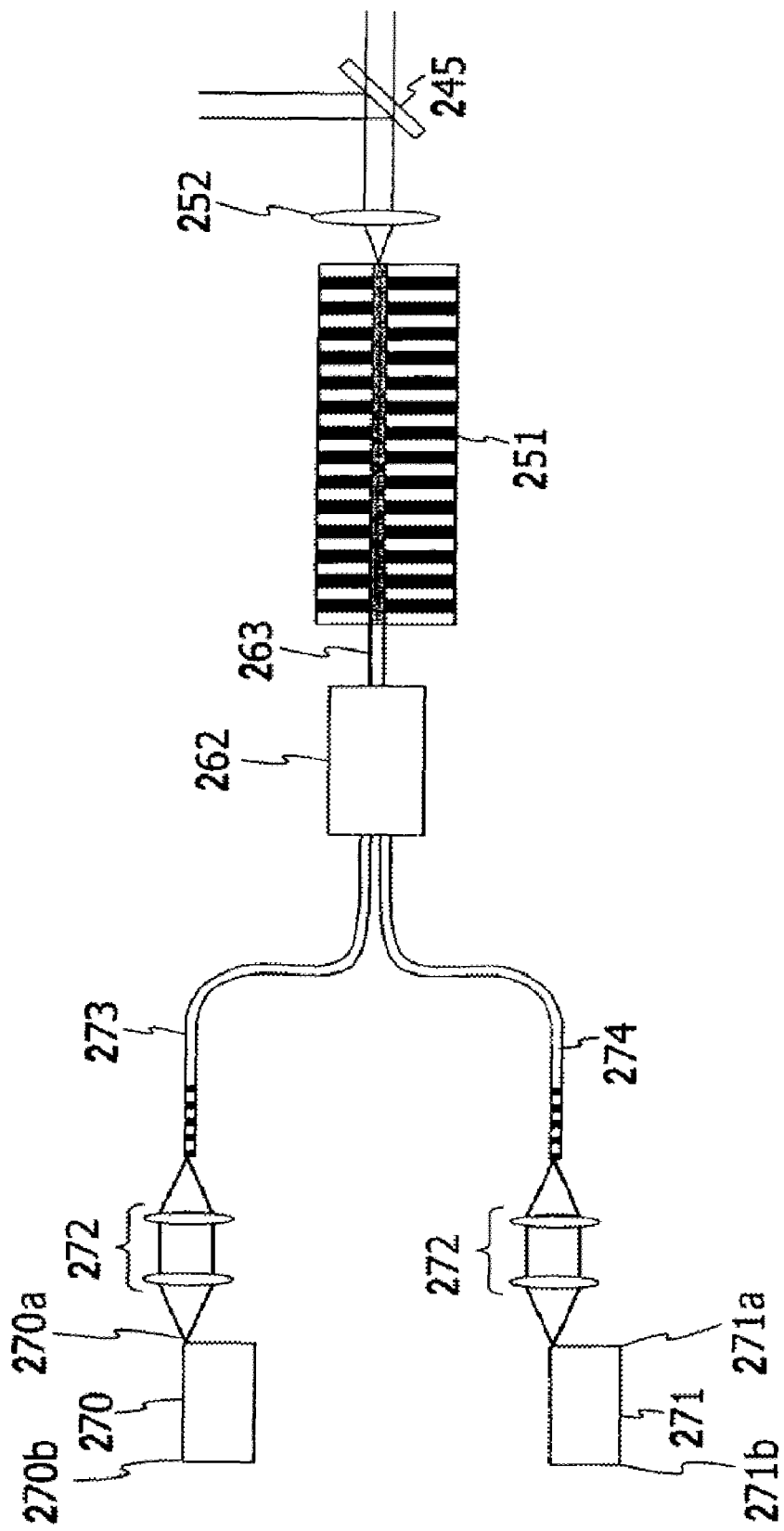
FIG. 13 is a block diagram of a laser light source in the yellow range according to Embodiment 2-5 of this invention.

FIG. 13 shows a laser light source in the yellow range according to Embodiment 2-5 of this invention. This is an example of further application of Embodiment 2-4. In excitation lasers 270, 271, AR coatings of a reflectance of 2% or less are applied on light-emitting side facets 270a, 271a and HR coatings of a reflectance of 90% or more is applied on opposite facets 270b, 271b. An output of the excitation laser 270 (271) is coupled, through a lens 272a (272b), to a polarization maintaining fiber (or single mode fiber) 273 (274) such that at its facet or at some midpoint therein a fiber Bragg grating was formed. Thus, resonators are constructed between the HR coating on the facet 270b (271b).

An oscillation wavelength of each laser is controlled by means of a reflection spectrum of the fiber Bragg grating. At this time, the central wavelengths of the reflection spectra of the fiber Bragg gratings are specified to be any one set of the following pairs.

940±10 nm, 1320±20 nm
980±10 nm, 1320±20 nm
1064±10 nm, 1320±20 nm
940±10 nm, 1550±30 nm

The linewidths (full widths at half maximum) are specified to be 0.3 nm or less.

Third Embodiment

In a method for generating mid-infrared light by difference frequency generation using a nonlinear optical crystal and two excitation laser beams, a relationship among the wavelengths $\lambda_1$, $\lambda_2$ of two excitation laser beams and the wavelength $\lambda_3$ of the generated mid-infrared light is given by the following formula.

[Formula 1]

$$\frac{1}{\lambda_3} = \frac{1}{\lambda_1} - \frac{1}{\lambda_2} \tag{3}$$

Here, the wavelength $\lambda_1$ may be larger or smaller than the wavelength $\lambda_2$. However, in order to satisfy $\lambda_3$>0 for convenience' sake, it is assumed that the wavelengths $\lambda_1$ and $\lambda_2$ satisfy: $\lambda_1 < \lambda_2$. In order to generate the difference frequency light $\lambda_3$ efficiently, the light needs to satisfy the following phase matching condition.

[Formula 2]

$$k_3 = k_1 - k_2 \tag{4}$$

In the formula (4), ki (i=1, 2, and 3) is a propagation constant of each laser beam propagating in the nonlinear crystal and satisfies the following formula with the refractive index of the nonlinear optical crystal at $k_i$ represented by $n_i$.

[Formula 3]

$$k_i = \frac{2\pi}{\lambda_i} n_i \tag{5}$$

However, it is generally difficult to satisfy the formula (4) due to a dispersion characteristic that a crystal possesses.

As a method for solving this, a quasi-phase matching method in which a nonlinear crystal is polarized and inversely polarized periodically is being used. For the quasi-phase matching method, ferroelectric crystals, such as $LiNbO_3$, are advantageous. Polarities of nonlinear optical constants of these crystals correspond to polarities of spontaneous polarization. When this spontaneous polarization is modulated with a period Λ in the propagation direction of light, the phase matching condition is expressed by the following formula.

[Formula 4]

$$k_3 = k_1 - k_2 - \frac{2\pi}{\Lambda} \tag{6}$$

When specific wavelengths $\lambda_1$, $\lambda_2$ are used as excitation beams, the formulas (3) and (6) can be satisfied simultaneously and hence the difference frequency light $\lambda_3$ can be generated efficiently.

However, when the wavelengths $\lambda_1$, $\lambda_2$ are varied to obtain a different wavelength $\lambda_3$ of the difference frequency light, if there is fluctuation in the wavelengths $\lambda_1$, $\lambda_2$, the three wavelengths no longer satisfy the formula (6) and the intensity of the difference frequency light $\lambda_3$ reduces. Here, a relationship among the wavelengths $\lambda_1$, $\lambda_2$, and $\lambda_3$, the period Λ, and the generation efficiency η of the difference frequency light is considered. First, the amount of phase mismatching Δk is defined as follows.

[Formula 5]

$$\Delta k = k_3 - k_1 + k_2 + \frac{2\pi}{\Lambda} \tag{7}$$

At this time, representing a sample length as l, the generation efficiency q of the difference frequency light depends on a product of Δk and l and is expressed by the following formula.

[Formula 6]

$$\eta = \eta_0 \frac{\sin^2\left(\frac{\Delta k l}{2}\right)}{\left(\frac{\Delta k l}{2}\right)^2} \tag{8}$$

In the formula (8), $\eta_0$ is a generation efficiency of the difference frequency light when Δk=0, and is determined by the nonlinear optical constant of a crystal, such as $LiNbO_3$, the excitation beam intensity, the sample length, etc. Therefore, in the same sample, since the period Λ is fixed, any change in either the wavelength $\lambda_1$ or the wavelength $\lambda_2$ increases or decreases Δk, bringing reduction in the generation efficiency η. Ranges of the wavelengths $\lambda_1$, $\lambda_2$ that give q=0.5$\eta_0$ for a given period Λ, that is, ranges that satisfy

[Formula 7]

$$\frac{\sin^2\left(\frac{\Delta k l}{2}\right)}{\left(\frac{\Delta k l}{2}\right)^2} \geq 0.5 \tag{9}$$

are called 3-dB ranges for the period Λ. If this 3-dB range can be widened, the wavelength of the difference frequency light $\lambda_3$ can be made variable without reducing the generation efficiency.

In the following discussion, a case where z-cut $LiNbO_3$ is used and the polarization directions of the two excitation beams and the difference frequency light all lie in the direction of c-axis of the crystal will be treated. At this time, the propagation characteristics of the two excitation beams and the difference frequency light are determined by the extraordinary ray refractive index $n_e$. $n_e$ is given by the Sellmeier's equation

[Formula 8]

$$n_e^2(\lambda) = \tag{10}$$
$$4.5567 - 2.605 \times 10^{-7} T^2 + \frac{0.097 + 2.7 \times 10^{-8} T^2}{\lambda^2 - (0.201 + 5.4 \times 10^{-8} T^2)^2} - 2.24 \times 10^{-2} \lambda^2$$

Here, T denotes temperature (K) and the wavelength $\lambda_3$ is expressed in μm.

Figure 14:
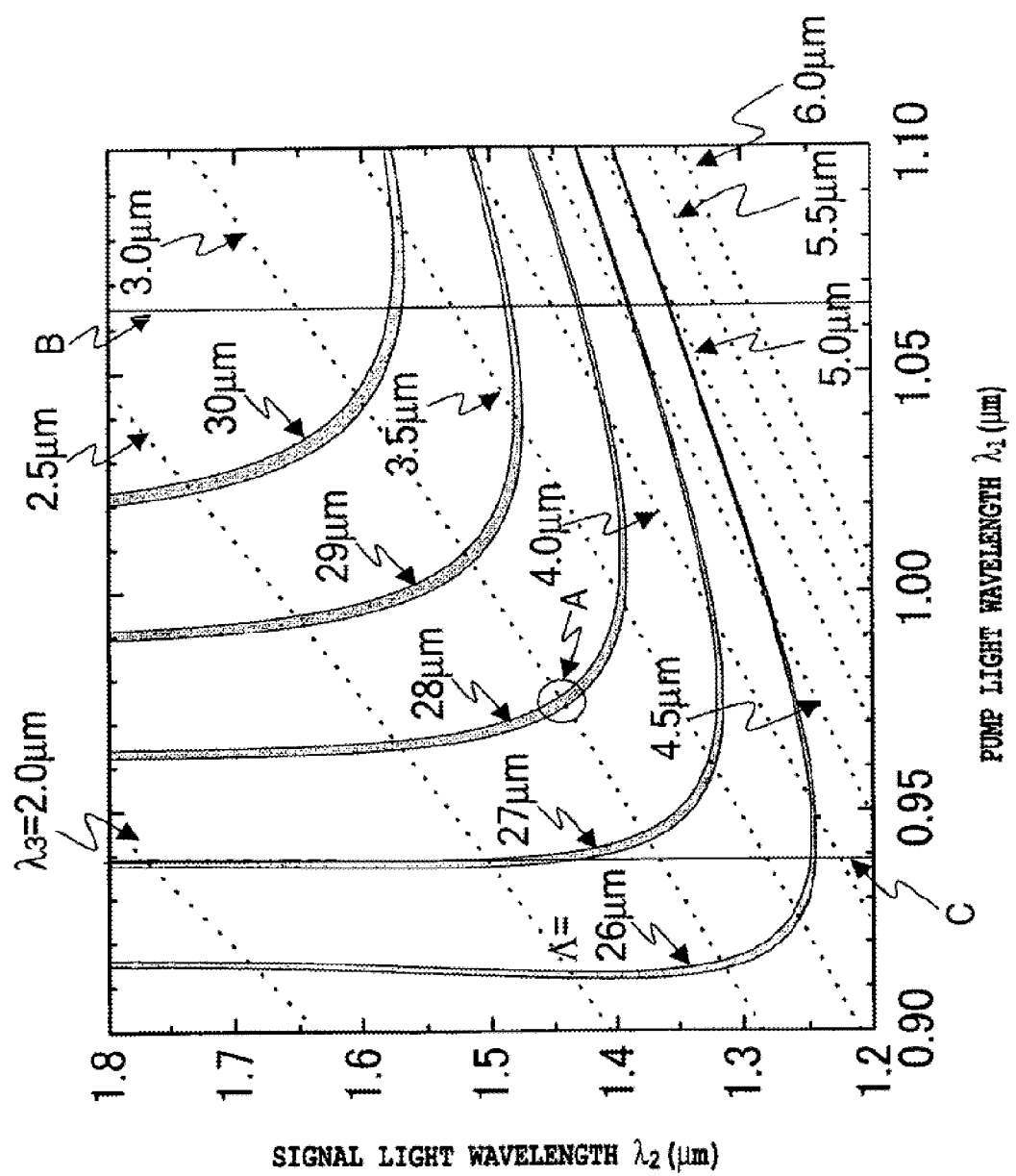
FIG. 14 is a diagram showing a 3-dB range with assumed values of the period $\Lambda$ for the wavelength $\lambda_3$ as a parameter.

FIG. 14 shows the 3-dB range obtained assuming the period Λ as several values with the wavelength $\lambda_3$ as a parameter. The 3-dB ranges of the wavelengths $\lambda_1$, $\lambda_2$ are given from the formulas (1), (5), and (7). The figure shows a relationship between the wavelengths $\lambda_1$, $\lambda_2$ by dotted lines that give the wavelengths $\lambda_3$ of the difference frequency light of 2.0 μm, 2.5 μm, 3.0 μm, 3.5 μm, 4.0 μm, 4.5 μm, 5.0 μm, 5.5 μm, and 6.0 μm calculated from the formula (3) at room temperature. Moreover, the 3-dB ranges for periods Λ=26 μm, 27 μm, 28 μm, 29 μm, and 30 μm are calculated by the formulas (7) and (9), and these ranges are shown by hatching. Device length was set to 10 mm.

A conversion efficiency of η=$\eta_0$ when the phase matching condition is completely satisfied exists in an almost middle part of the 3-dB range. That is, in difference frequency generation in $LiNbO_3$ that has the periodically poled structure of a period Λ, the quasi-phase matching element of a period Λ is used. In the case where a desired difference frequency light $\lambda_3$ is obtained, the wavelengths $\lambda_1$, $\lambda_2$ to achieve η=0.5$\eta_0$ are obtained from the formulas (3), (7), and (9), and the 3-dB range for the period Λ is given by intersections of the curves of the formula (3) that gives the desired difference frequency light $\lambda_3$.

As an example, consider a case where the difference frequency light of a wavelength $\lambda_3$=3.0 μm is generated using $LiNbO_3$ having the periodically poled structure of a period Λ=28 μm. A range of the wavelengths $\lambda_1$, $\lambda_2$ where a dotted line of a wavelength $\lambda_3$=3.0 μm and the 3-dB range of a period Λ=28 μm intersect (a part that is circled and designated by a symbol A) give η=0.5$\eta_0$.

Next, concrete conditions will be shown. The generation intensity in difference frequency generation is proportional to a product of two excitation beam intensities. Because of this, the Nd-YAG laser (wavelength of 1.064 μm) that can easily achieve high intensity was mainly used in hitherto reported examples. Here, the case where the wavelength $\lambda_1$ is fixed as $\lambda_1$=1.064 μm and the wavelength $\lambda_2$ is varied to achieve tunable difference frequency light $\lambda_3$ is considered. When $LiNbO_3$ having the periodically poled structure of a period Λ is used, η=0.5 $\eta_0$ is achieved at the wavelength $\lambda_2$ in a range where the 3-dB range of a period Λ shown by hatching in FIG. 14 and a straight line B of a wavelength $\lambda_1$=1.064 μm intersect.

Figure 15:
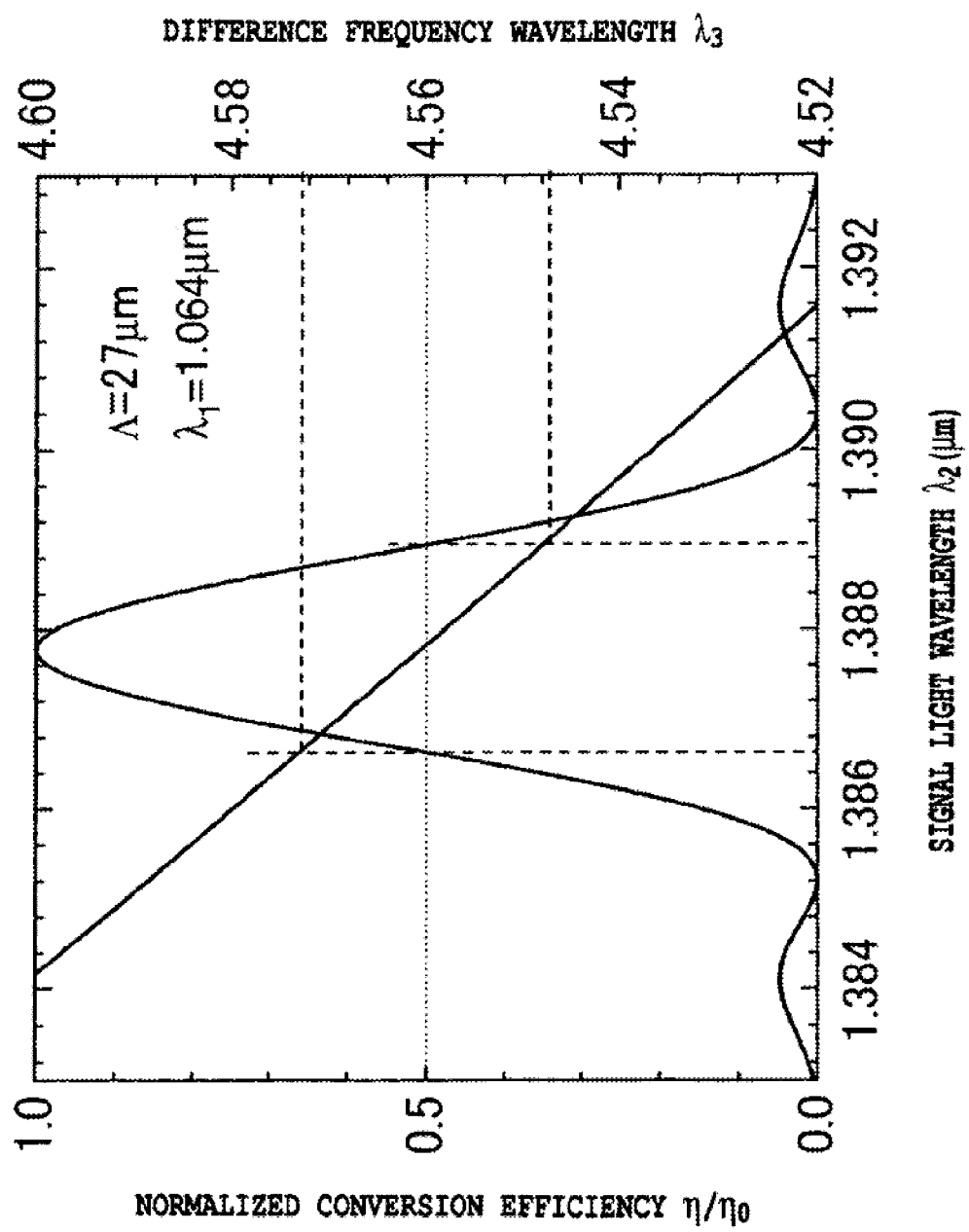
FIG. 15 is a diagram showing normalized conversion efficiency $\eta/\eta_0$ as a function of the wavelength $\lambda_2$ when the period and the wavelength are set as $\Lambda=27$ μm and $\lambda_1=1.064$ μm, respectively.

FIG. 15 shows normalized conversion efficiency η/$\eta_0$ as a function of the wavelength $\lambda_2$ when a period Λ=27 μm and a wavelength $\lambda_1=1.064$ μm are set, respectively. The width of the wavelength $\lambda_2$ that satisfies $\eta=0.5\eta_0$ is only about 2 nm, and consequently the amount of tunability of the difference frequency light $\lambda_3$ is limited to about 20 nm. In addition, when the period Λ is changed to any of 28 μm, 29 μm, and 30 μm, as long as a wavelength $\lambda_1=1.064$ μm is assumed, the width of a wavelength $\lambda_2$ that satisfies $\eta=0.5\ \eta_0$ is only about 2 nm in any case; therefore, the amount of tunability of the difference frequency light $\lambda_3$ is limited similarly.

However, examination of FIG. 14 indicates that there is a range where a tunable range of the difference frequency light $\lambda_3$ can be widened considerably if the wavelength $\lambda_1$ is fixed and the wavelength $\lambda_2$ is varied. That is, if the straight line indicating a constant wavelength $\lambda_1$ and the 3-dB range of a period Λ intersect in a wider range, the tunable range width of the difference frequency light $\lambda_3$ will increase dramatically. The 3-dB range of a period Λ=25.5–29 μm is almost parallel to the vertical axis at a wavelengths $\lambda_1$ of 0.9-1.0 μm, and accordingly intersects widely the straight line indicating a constant wavelength $\lambda_1$ in this wavelength band of 0.9-1.0 μm. That is, even if using the periodically poled structure LiNbO$_3$ having a single period Λ, when the wavelength $\lambda_1$ is fixed in the range of 0.9-1.0 μm and the wavelength $\lambda_2$ is varied in the range of 1.3-1.8 μm, the difference frequency light $\lambda_3$ can be tuned efficiently satisfying the phase matching condition in almost whole range of 1.3 μm<$\lambda_2$<1.8 μm.

For example, when a period Λ=27 μm and a wavelength $\lambda_1=0.94$ μm are set, the normalized conversion efficiency for a wavelength $\lambda_2$ becomes $\eta=0.5\eta_0$ in the wavelength band of $\lambda_2$>1.43 μm and the difference frequency light can be generated in a wide wavelength band of almost 2-3 μm. In addition, near the wavelength $\lambda_3=3$ μm, it becomes possible to generate it with a single period Λ by temperature adjustment, as will be described later.

As explained above, the laser light source equipped with the first laser, the second laser, and the nonlinear optical crystal having the periodically poled structure of a single period can tune the laser beam in the mid-infrared region so as to be in the wavelength band of 2-3 μm by changing the wavelength of one of the lasers.

Embodiment 3-1

Figure 16:
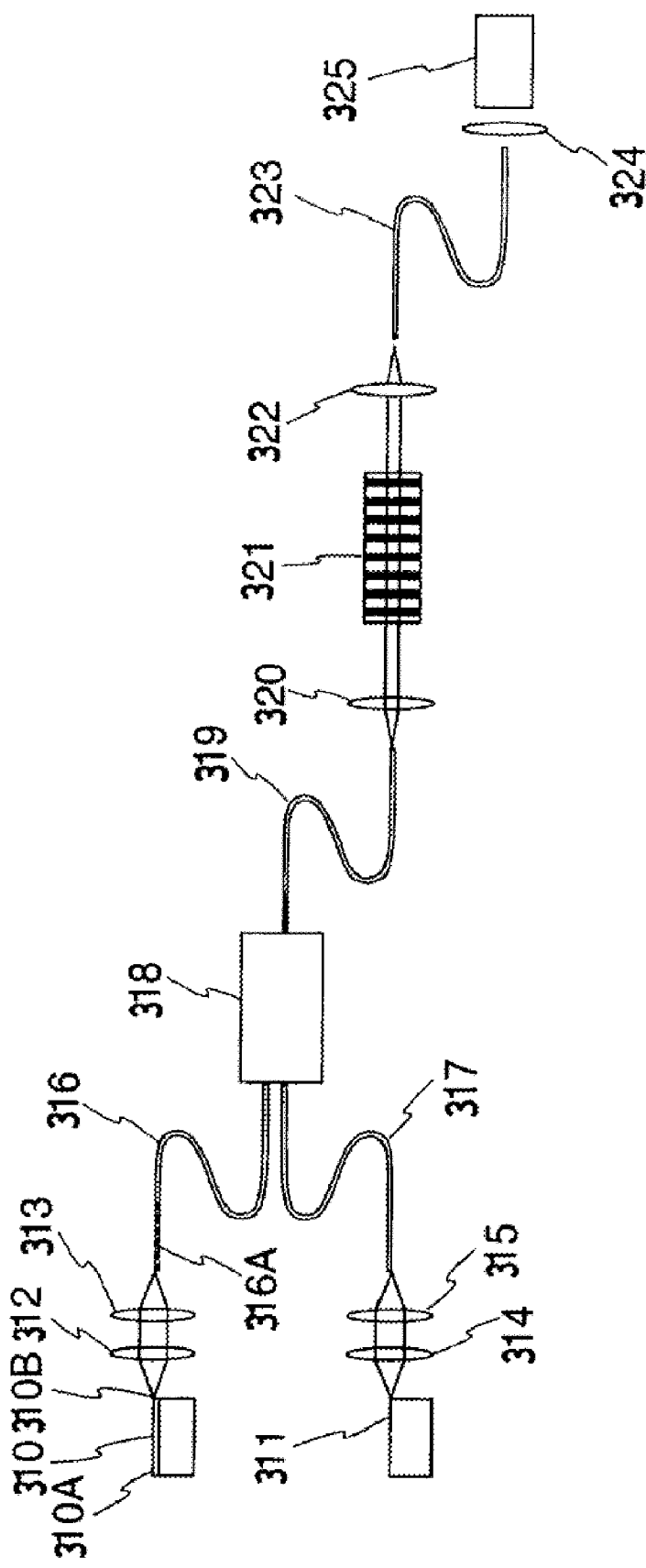
FIG. 16 is a block diagram showing a laser light source for generating mid-infrared light according to one embodiment of this invention.

FIG. 16 shows a laser light source for generating mid-infrared light according to one embodiment of this invention. The laser light source comprises: a semiconductor laser 310 of a wavelength $\lambda_1$ ($\lambda_1$ is specified to be in a 0.94 μm wavelength band); a semiconductor laser 311 of a wavelength $\lambda_2$ ($\lambda_2$ is specified to be in 1.45-1.60 μm wavelength band and tunable); a multiplexer 318 for multiplexing the output beams of the semiconductor lasers 310,311; and a LiNbO$_3$ bulk crystal 321 with the periodically poled structure of a single period that allows the multiplexed beams to enter thereinto and generates the difference frequency light, i.e., mid-infrared light. The output of the semiconductor laser 310 is connected to the multiplexer 318 through a coupling lens system 312,313 and a polarization maintaining fiber 316. The output of the semiconductor laser 311 is connected to the multiplexer 318 through a coupling lens system 314,315 and a polarization maintaining fiber 317.

In the semiconductor laser 310, a high reflective film of a reflectance of 90% or more is formed on its facet 310A, and a low reflective film of a reflectance of 2% or less is formed on its opposite facet 310B. The polarization maintaining fiber 316 is provided with a fiber Bragg grating 316A, so that the wavelength stability is improved. It is further possible to connect a fiber amplifier in the middle of the polarization maintaining fiber 317, as needed, to boost the output light of the semiconductor laser 311.

The output of the multiplexer 318 is connected to the LiNbO$_3$ bulk crystal 321 through an optical fiber 319 and a coupling lens system 320. Incidentally, the output of the LiNbO$_3$ bulk crystal 321 is connected to a spectrometer 325 through a coupling lens system 322,324 and an optical fiber 323 in order to measure the output beam that is mid-infrared light.

As shown by the straight line C in FIG. 14, when a wavelength $\lambda_1$ is specified to be in the 0.94-μm wavelength band, and when a period Λ of the LiNbO$_3$ bulk crystal 321 is 27 μm, the aforesaid 3-dB range can be obtained with a single period Λ even if the wavelength of the semiconductor laser 311 is varied in the range of 1.45-1.60 μm. In other words, mid-infrared light can be obtained in the wide wavelength band with a single period Λ. The figure shows that with a wavelength $\lambda_1$ in the 0.94-μm wavelength band, when the wavelength $\lambda_2$ is varied in the range of 1.45 μm to 1.60 μm, the wavelength $\lambda_3$ of generated mid-infrared light will cover a wide range of 2.3-2.7 μm.

Figure 17:
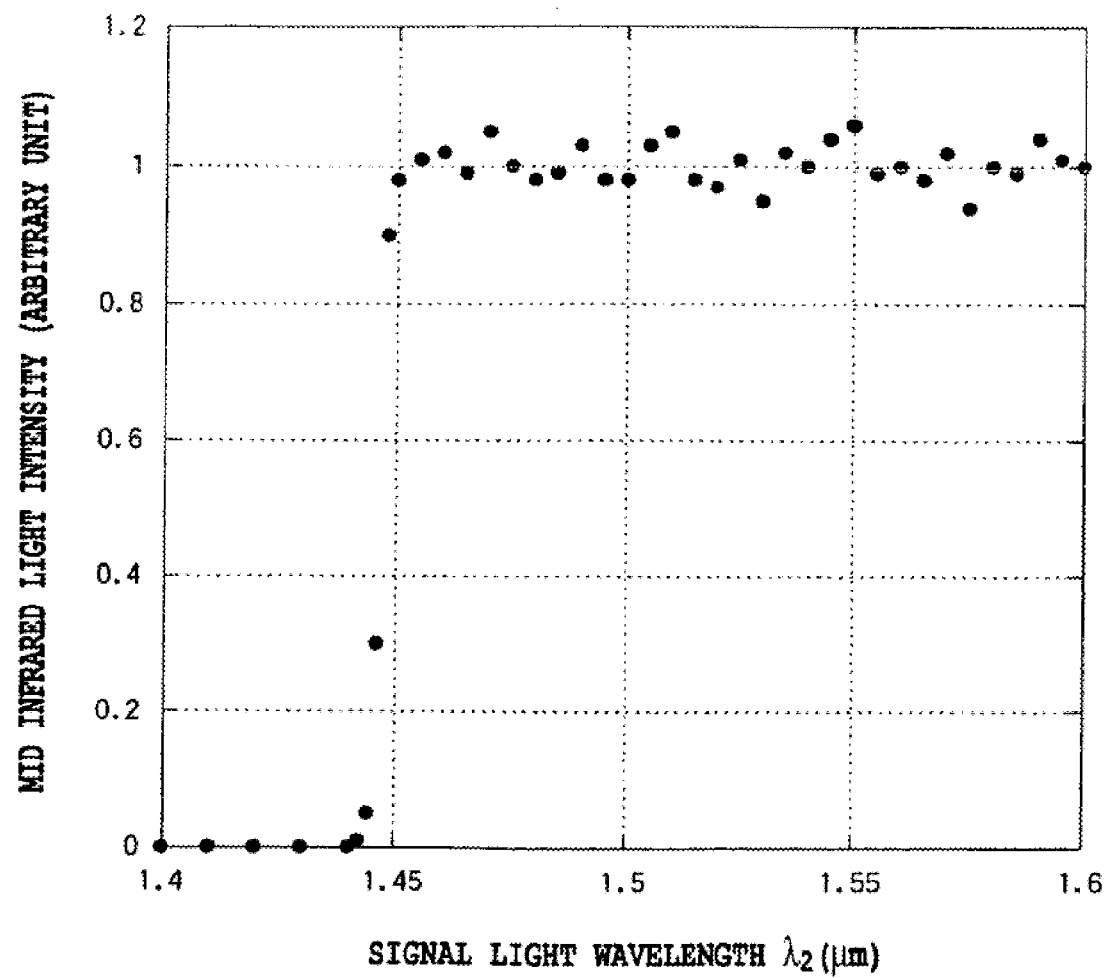
FIG. 17 is a diagram showing the 3-dB range in Embodiment 3-1.

FIG. 17 shows the 3-dB range in Embodiment 1. The vertical axis indicates mid-infrared light intensity, and the horizontal axis indicates the wavelength $\lambda_2$ of the semiconductor laser 311. As can be expected from calculation results in FIG. 14, with the LiNbO$_3$ bulk crystal 321 having a single period Λ, mid-infrared light with almost constant intensity can be obtained in a wide wavelength band of 1.45 μm<$\lambda_2$<1.60 μm. The output of the semiconductor laser 311 is constant in the whole wavelength band. A variation of 1.45 μm<$\lambda_2$<1.60 μm corresponds to a variation of 2.7 μm>$\lambda_3$ of mid-infrared light >2.3 μm. The wavelength of generated mid-infrared light is checked with the spectroscope 325. In this embodiment, the LiNbO$_3$ bulk crystal 321 of a device length of 10 mm was used. The conversion efficiency was 1%/W in the whole wavelength band.

In the case where a difference-frequency-generation experiment like this embodiment is conducted, maximum mid-infrared light is generated when polarization directions of the two excitation beams coincide with each other. Here, if the polarization direction of the semiconductor laser 310 is inclined by an angle θ while the polarization direction of the semiconductor laser 311 is fixed, the light intensity $I_3$ of the mid-infrared light will be expressed by the following formula, using the light intensity of the semiconductor laser 310 represented by $I_1$ and the light intensity of the semiconductor laser 311 represented by $I_2$,

[Formula 9]

$$I_3 \propto I_1 I_2 \cos^2\theta \quad (11)$$

Figure 18:
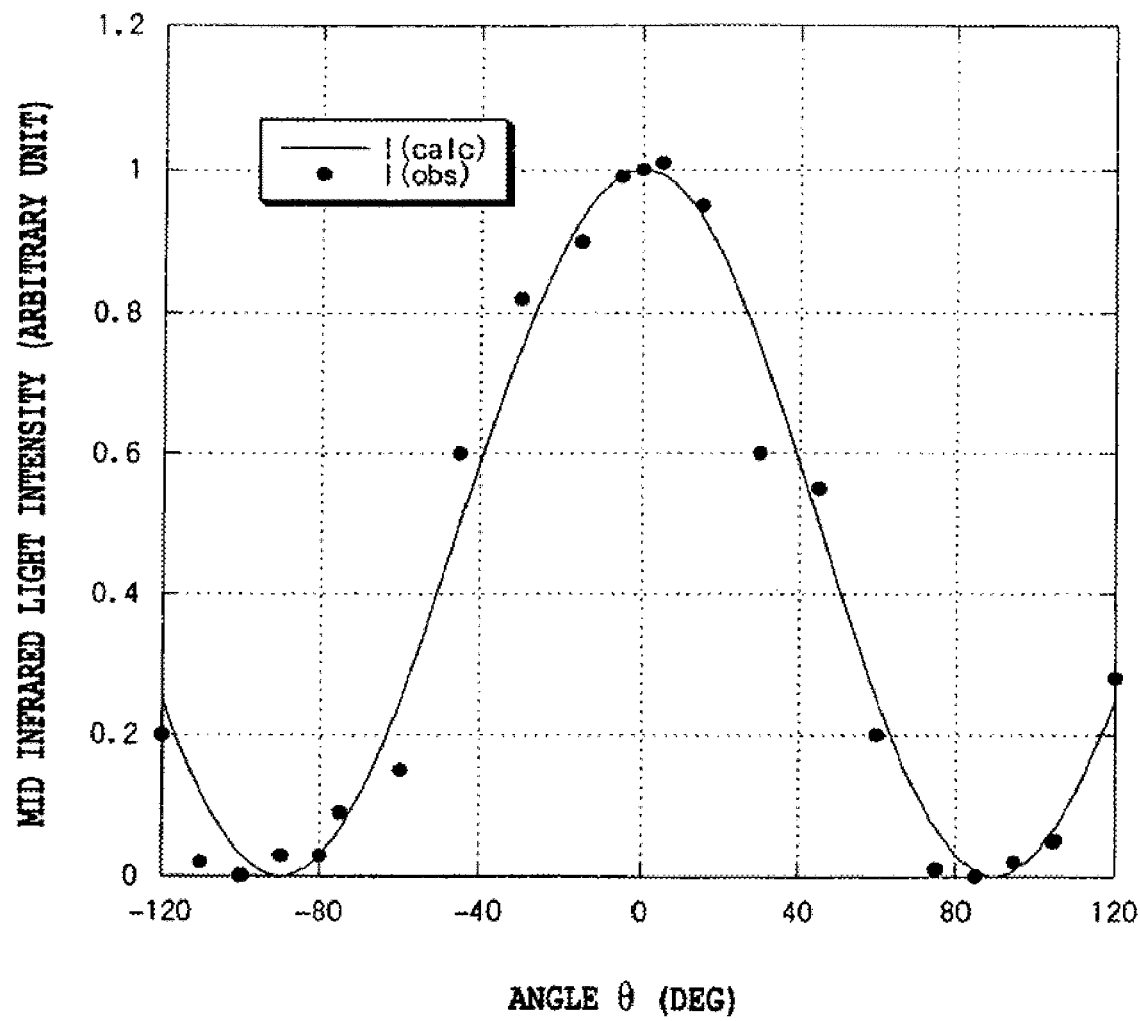
FIG. 18 is a view showing the polarization dependency of mid-infrared light outputted in Embodiment 3-1.

The formula (11) can be used as means for checking the generation of the mid-infrared light. FIG. 18 shows polarization dependency of the mid-infrared light outputted in Embodiment 3-1. It was confirmed that an experimental result was mostly in agreement with what was obtained by calculation.

Embodiment 3-2

In Embodiment 3-1, the wavelength band of the outputted mid-infrared light was 2.3-2.7 μm. However, the wavelength band can be expanded further by changing the period Λ of the LiNbO$_3$ crystal. In Embodiment 3-2, the period Λ of the LiNbO$_3$ bulk crystal 321 shown in FIG. 16 was set to 26 μm. The semiconductor laser 310 was specified to be a device capable of tuning its wavelength in a very small range in a 0.91-μm wavelength band, and the semiconductor laser 311 was specified to be a device capable of tuning its wavelength in a wide range in the wavelength band of 1.30-1.68 μm.

This device can deliver mid-infrared light having almost constant intensity in as wide a 3-dB range as the wavelength band of 1.30 μm<$\lambda_2$<1.68 μm with the LiNbO$_3$ bulk crystal 321 that uses only one period Λ. Since the wavelength $\lambda_2$ was varied in the range of 1.30-1.68 μm, the wavelength $\lambda_3$ of the mid-infrared light in a range of 3.1-2.0 μm was able to be obtained. In this embodiment, the LiNbO$_3$ bulk crystal 321 of a device length of 10-mm was used. The conversion efficiency was 1%/W in the whole wavelength band.

Note that the refractive index of LiNbO$_3$ crystal varies with temperature, as can be seen from the formula (10), and consequently the effective period Λ also varies with this. Therefore, if the temperature of LiNbO$_3$ crystal is adjusted minutely, the effective one period Λ can be varied. Therefore, even when the difference frequency generation is performed in a LiNbO$_3$ crystal having a single period Λ, high conversion efficiency can be maintained. As shown in FIG. 14, there is a range in which the conversion efficiency cannot be maintained high if the wavelength of the semiconductor laser 310 is fixed (for example, a range in which the characteristic curve is not in parallel completely to the vertical axis as in the case of a period Λ=28.29 μm). In this connection, if the temperature of the LiNbO$_3$ bulk crystal 321 is adjusted so that the effective period Λ to the wavelength of the semiconductor laser 310 is optimized, the high conversion efficiency can always be maintained.

In Embodiment 3-2, the period Λ was varied by a step of 0.1 μm between 25.5 μm and 29.3 μm under a suitable temperature adjustment and a beam of the difference frequency is generated using the LiNbO$_3$ bulk crystal 321 having a period Λ. As a result, when a wavelength $\lambda_1$ is suitably selected in the range of 0.9-1.0 μm for each period Λ and the wavelength $\lambda_2$ is varied in the range of 1.27-1.80 μm according to this, the wavelength $\lambda_3$ of the mid-infrared light can be continuously obtained in the range of 3.1-2.0 μm. However, in the period Λ exceeding 28.5 μm, a portion in the characteristics curve parallel to the vertical axis tends to decrease, as shown in FIG. 14. Therefore, contribution of the temperature control necessary to obtain a beam of the difference frequency of a constant intensity becomes large gradually with the period Λ. A temperature change of 100° C. corresponded to a change as much as 0.005 μm of the wavelength $\lambda_1$.

Embodiment 3-3

If a wavelength converter element is changed to a waveguide type from LiNbO$_3$ crystal of the bulk type and the wavelength converter is configured in the same manner as Embodiments 3-1 and 3-2, mid-infrared light can be obtained more efficiently. Embodiment 3-3 used an optical system such that the LiNbO$_3$ bulk crystal 321 shown in FIG. 16 was changed to a waveguide element. The device length of the LiNbO$_3$ waveguide was set to 10 mm, a cross-sectional size of the core was set to 8 μm×8 μm, and the period Λ was set to 26 μm. The semiconductor laser 310 was specified to be tunable in a very small range in the 0.91-μm wavelength band, and the semiconductor laser 311 was specified to be tunable in a wide range in the wavelength band of 1.3-1.65 μm.

Regarding the 3-dB range in the waveguide element, mid-infrared light $\lambda_3$ having an almost constant intensity was obtained in the wavelength band of 3.1-2.0 μm for $\lambda_1$ in the 0.91-μm wavelength band and for $\lambda_2$ in a wide wavelength band of 1.3 μm<$\lambda_2$<1.65 μm under an appropriate temperature adjustment. The conversion efficiency was improved in the whole wavelength band, showing improvement by two orders of magnitude compared to the bulk element.

Moreover, the period Λ was changed in a range of 25.5-29.3 μm by a step of 0.1 μm, and the mid-infrared light was generated under suitable temperature adjustment using a LiNbO$_3$ waveguide having a period Λ. The result shows that the wavelength $\lambda_3$ of the mid-infrared light can be continuously obtained in the range of 3.1-2.0 μm when the wavelength $\lambda_1$ is suitably selected from a range of 0.9-1.0 μm for each period Λ and the wavelength $\lambda_2$ is varied in the range of 1.27-1.80 μm according to the wavelength $\lambda_1$.

Embodiment 3-4

As shown in FIG. 14, the phase matching curve has an area in which the curve makes an abrupt bend. The use of this area does not give a large merit particularly in terms of wavelength tunability. However, in performing the difference frequency generation, the tolerance of wavelength stability in each of the two excitation beams is improved largely, especially bringing an effect for improvement in the tolerance of a short wavelength-side semiconductor laser. For example, in FIG. 14, in the case of a period Λ=27 μm, for the wavelength $\lambda_2$ of the semiconductor laser 311 in the range of 1.45-1.8 μm, when the wavelength $\lambda_2$ varies, the wavelength $\lambda_2$ will not go out of the 3-dB range. On the other hand, when the wavelength $\lambda_1$ of the semiconductor 310 varies even slightly, it will cause the wavelength $\lambda_3$ to go out of the 3-dB range. However, when the wavelength $\lambda_2$ is in a curved part near 1.35 μm, there arises an advantage that the tolerance in the wavelength variation for the 3-dB range is doubled also for the wavelength $\lambda_1$ that is a half of the wavelength $\lambda_2$. At the same time, the amount of temperature adjustment of the LiNbO$_3$ bulk crystal 321 also decreases. Here, note that the tolerance for the wavelength $\lambda_2$ decreases in this case, but still keeps a sufficient width from the point of view of the stability of the commercially available normal laser light source.

Embodiment 3-4 uses an optical system in which the reflective films on the facets 310A, 310B of the semiconductor laser 310A and the fiber Bragg grating 316A of the polarization maintaining fiber 316 are removed from the previously described optical system. The fiber Bragg grating is the device with which a beam of the designed wavelength can be obtained selectively, and was used to suppress the variation in the wavelength $\lambda_1$ in Embodiment 3-1. Therefore, when the fiber Bragg grating 316A is removed, there might be a case where a stable 3-dB range is hard to obtain. However, in Embodiment 3-4, the laser light source can perform sufficiently stable operation, not getting out of the 3-dB range, even without a configuration for stabilizing the wavelength like this. In this embodiment, the period Λ of the LiNbO$_3$ bulk crystal 321 was set to 27 μm, the wavelength of the semiconductor laser 310 was set to 0.945 μm, and the wavelength of the semiconductor laser 311 was set to 1.35 μm.

Embodiment 3-5

With use of a laser light source for generating mid-infrared light according to this invention, NO$_x$ that is an environmental gas can be detected accurately. Since the fundamental absorption of NO$_x$ gas exists in a wavelength of longer than 5 μm, it is convenient to use the following reaction formulas to detect it, considering the absorption property of LiNbO₃ (light of a wavelength of 5.4 μm or more hardly pass through LiNbO₃).

That is, since NO$_x$ is decomposed by NH₃ with a catalyst, concentrations of NO and NO$_x$ can be calculated indirectly by checking the quantity of consumed NH3 or the quantity of newly generated H₂O. Moreover, a fact that overtones of the fundamental absorption of NO and NO₂ reside in the wavelengths of 2-3 μm can be used to detect them. Then, if there is a laser light source that is tunable in wavelengths of 2-3 μm, the aforesaid absorption of the gases can be checked together. The major fundamental absorption wavelength, the wave number, and the name of absorption of gases are as follows.

H₂O: 2.662 μm, 3756 cm⁻¹, anti-symmetry stretching vibration

H₂O: 2.734 μm, 3657 cm⁻¹, totally symmetry stretching vibration

NH₃: 2.904 μm, 3444 cm⁻¹, double degenerated vibration

NH₃: 2.997 μm, 3337 cm⁻¹, totally symmetry vibration

NO: 5.330 μm, 1876 cm⁻¹, anti-symmetry stretching vibration, overtone=2.665 μm

NO₂: 6.180 μm, 1618 cm⁻¹, anti-symmetry stretching vibration, overtone=3.090 μm

Figure 19:
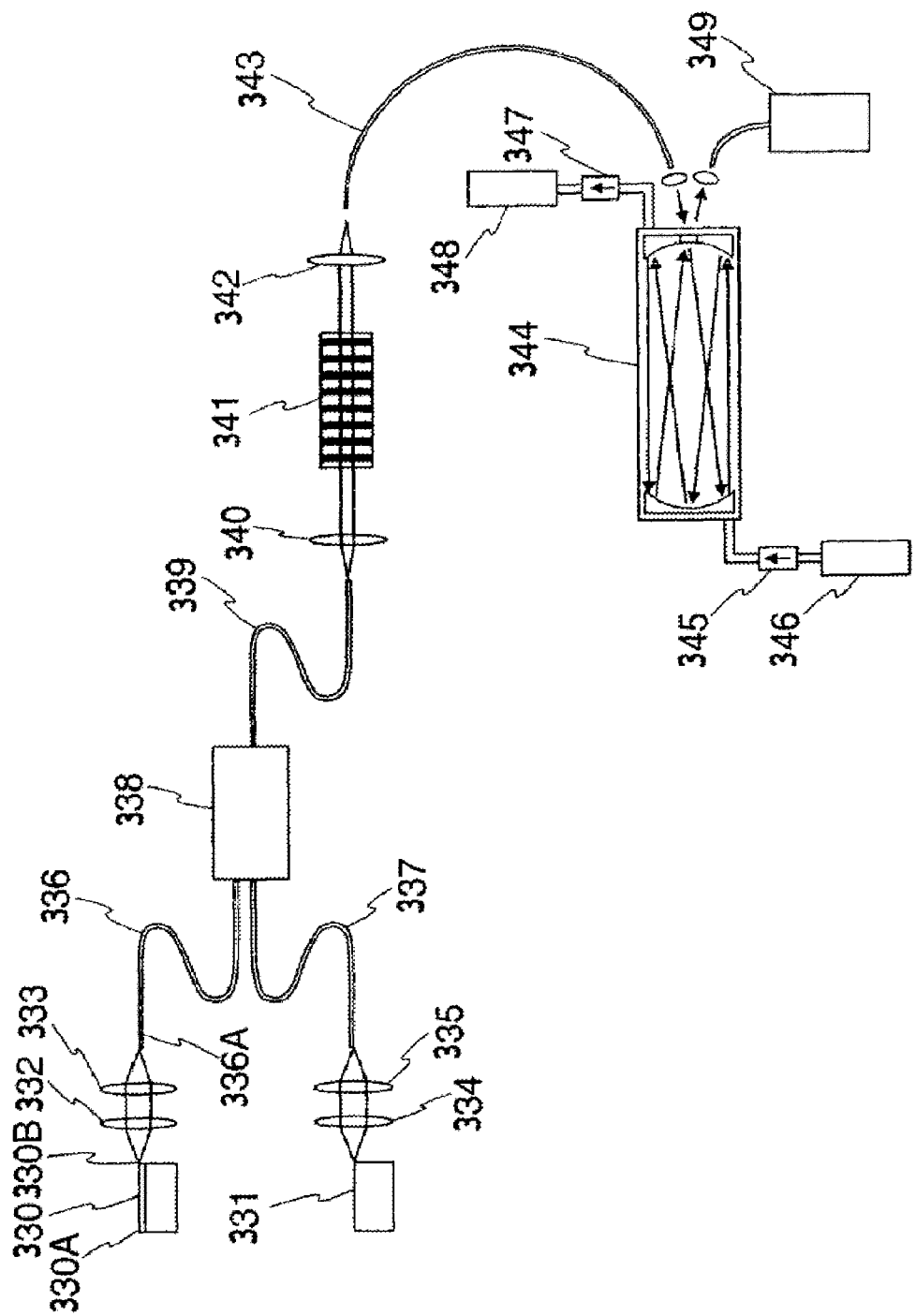
FIG. 19 is a block diagram showing an optical absorption analyzer according to one embodiment of this invention.

FIG. 19 shows an optical absorption analyzer according to one embodiment of this invention. This figure particularly shows an optical system for detecting NO$_x$ gas concentration. A gas cell 344 in which a measured gas is enclosed has an optical path length of up to 18 m using reflectors on both ends thereof. A reactive gas is led into the gas cell 344 from a gas removal tube 346 and discharged to a gas exhaust tube 348 by a pump 347. When the pump is employed, the pressure in the gas cell can be changed. In the gas removal tube 346, NO$_x$ is removed by reactions of formula (12) or (13). A detector 349 is a HgCdTe detector for mid-infrared light.

The laser light source comprises: a semiconductor laser 330 of a wavelength λ₁ (λ₁ is specified in the 0.94-μm wavelength band, fixed); a semiconductor laser 331 of a wavelength λ₂ (λ₂ is specified in the range of 1.28-1.46 μm, tunable), a multiplexer 338 for multiplexing the output beams of the semiconductor lasers 330, 331, and a LiNbO₃ bulk crystal 341 of a period Λ=26 μm that generates mid-infrared light. The output of the semiconductor laser 330 is connected to the multiplexer 338 through a coupling lens system 332, 333 and a polarization maintaining fiber 336, and the output of the semiconductor laser 331 is connected to the multiplexer 338 through a coupling lens systems 334, 335 and a polarization maintaining fiber 337.

In the semiconductor laser 330, a high reflective film of a reflectance of 90% or more is formed on its facet 330A, and a low reflective film of a reflectance of 2% or less is formed on its opposite facet 330B. The polarization maintaining fiber 336 is provided with a fiber Bragg grating 336A, so that the wavelength stability is improved. The output of the multiplexer 338 is connected to the LiNbO₃ bulk crystal 341 through an optical fiber 339 and a coupling lens system 340. The output of the LiNbO₃ bulk crystal 341 is connected to a gas cell 344 through a coupling lens system 342 and an optical fiber 343.

In the description of Embodiment 3-5, first measurement results accompanying removal of NO₂ gas will be shown. The measurement is performed after dividing it into the following three stages.

(i) Only NO₂ gas is introduced into the gas removal tube without giving a catalyst and NH₃ gas.

(ii) NO₂ gas is introduced into the gas removal tube without giving a catalyst while NH₃ gas is given.

(iii) NO₂ gas is introduced into the gas removal tube while a catalyst and NH₃ gas are given.

The stage (iii) corresponds to a state where no chemical reaction occurs when the wavelength of the semiconductor laser 331 is adjusted to 1.290 μm, and overtone absorption of the anti-symmetry stretching vibration of NO₂ can be detected at a wavelength 3.090 μm. On the other hand, even when the wavelength of the semiconductor laser 331 is adjusted again to match absorption wavelengths of NH₃ or H₂O, absorptions of these two gases are not observed.

In the stage (ii), even when NH₃ is given, no chemical reaction progresses because there is no catalyst, so absorptions of unreacted NO₂ and NH₃ will be observed. However, in the stage (iii), since a catalyst is given, a chemical reaction will progress; NO₂ will be removed and NH₃ will be consumed. Consequently, absorptions of NO₂ and NH₃ start to decrease, and absorption of newly generated H₂O will be observed instead. When more NH₃ is added, the absorption of NO will disappear completely and absorptions of NH₃ added superfluously and newly generated H₂O will increase.

Here, the use of the formula (13) enables the concentration of NO₂ to be measured quantitatively in the stage (iii). That is, as a large quantity of NH₃ is being added gradually, absorption of NO₂ will decrease, and absorptions of NH₃ added superfluously and newly generated H₂O will appear. The concentration of NO₂ can be calculated with the formula (1.3) by measuring the quantity of NH₃ that is added up to any one of the following points: a point at which the absorption of N₂O becomes zero, a point at which the absorption of superfluous NH₃ starts to appear; and a point at which the absorption intensity of H₂O starts to take a constant value after it increased.

Since for the concentration of NH₃, only the quantity of addition should be measured, measurement can be done correctly. In Embodiment 3-5, when the LiNbO₃ bulk crystal 341 of a length of 10 mm was used, the minimum detection concentration of NO₂ was 1 ppm at 100 Torr. When the waveguide of a length of 10 mm was used, the minimum detection concentration of NO₂ was able to be reduced to the order of 10 ppb.

The detection of NO gas is also done conveniently using the formula (12). The concentration of NO can be calculated by measuring the quantity of NH₃ that is added to any one of the following points: a point at which the absorption of NO becomes zero when NH₃ and O₂ are being added to the gas removal tube 346 gradually, a point at which the absorption of superfluous NH₃ starts to appear; and a point at which the absorption intensity of H₂O starts to take a constant value after it increased (here, the absorption of O₂ is not observed). Note however that, since the wavelength of overtone absorption of NO and the wavelength of anti-symmetry stretching vibration absorption of H₂O are very close to each other, totally symmetry stretching vibration absorption of H₂O and the absorption of NH₃ will mainly be employed. The minimum detection concentration of NO gas was almost in the same level as NO₂ gas.

In addition, since it is only necessary to prepare a single period Λ for the LiNbO₃ bulk crystal 341 in Embodiment 3-5, the measurement is extremely simple and quick. Moreover, if what is required is to check the existence of NO and NO₂ gases, the measurement will become simpler and quicker, because it is only necessary to check the existence of a absorption peak and it is not necessary to measure the quantity of NH₃.

Embodiment 3-6

In wavelengths of 2-3 μm, when a gas meter for gases of $NO_x$, $CO_2$, CO, etc. is constructed with a tunable laser light source in the mid-infrared region, gas concentrations of multiple kinds of gases can be measured with a single unit of light source. Here, given is a description of how to detect simultaneously four kinds of gases: NO, $NO_2$, CO, and $CO_2$. The fundamental absorption wavelength, the wave number, the name of absorption, and the overtone absorption wavelength of targeted gases are as follows.

$CO_2$: 4.257 μm, 2349 cm$^{-1}$, anti-symmetry stretching vibration, overtone=2.129 μm CO: 4.666 μm, 2143 cm$^{-1}$ stretching vibration, overtone=2.333 μm NO: 5.330 μm, 1876 cm$^{-1}$, anti-symmetry stretching vibration, overtone=2.665 μm $NO_2$: 6.180 μm, 1618 cm$^{-1}$; anti-symmetry stretching vibration, overtone=3.090 μm $H_2O$: 2.662 μm, 3756 cm$^{-1}$, anti-symmetry stretching vibration H—O: 2.734 μm, 3657 cm$^{-1}$, totally symmetry stretching vibration $NH_3$: 2.904 μm, 3444 cm$^{-1}$, double degenerated vibration $NH_3$: 2.997 μm, 3337 cm$^{-1}$, totally symmetry vibration In this embodiment, gases are made to pass through the following three stages, where each gas is removed one by one, and the gas concentration of each gas was measured. The configuration is the same as that of Embodiment 3-5 shown in FIG. 19.

(a) NO, $NO_2$, $CO_2$, and CO gases are introduced into a gas removal tube without giving a catalyst and a gas for removable.

(b) A catalyst and $NH_3$ and $O_2$ gases are given to the gases to remove NO and $NO_2$ gases.

(c) After NO and $NO_2$ gases were removed in the (b), $O_2$ gas is given to burn CO gas.

In the stage (a), since no chemical reaction progresses in the gas removal tube 346, overtone absorption of NO, $NO_2$, $CO_2$, and CO gases is observed in wavelengths of 2-3 μm.

When the gases enter the stage (b), NO and $NO_2$ gases are removed and $NH_3$, gas is consumed, and in response to it, absorption of these gases starts to decrease and absorption of newly generated $H_2O$ will be observed. When surplus $NH_3$ and $O_2$ gases are added, absorption of NO and $NO_2$ gases will disappear completely and absorption of surplus $NH_3$ gas and newly generated $H_2O$ gas will increase (also in this stage, absorption of $O_2$ is not observed). In the stage (c), as CO gas is combusted according to the following reaction formula (14), absorption of $CO_2$ will increase.

$$2CO + O_2 \rightarrow 2CO_2 \qquad (14)$$

In the stage (b), total concentrations of NO and $NO_2$ can be measured quantitatively. That is, when a large quantity of $NH_3$ and $O_2$ are being added, absorption of NO and $NO_2$ will decrease, and absorption of $NH_3$ added superfluously and newly generated $H_2O$ will appear. Total concentrations of NO and $NO_2$ contained in the gas removal tube can be calculated with the formulas (12) and (13), if measuring the quantity of $NH_3$ that is added up to any one of three points: a point at which the absorptions of NO and $NO_2$ become zero, a point at which the absorption of surplus $NH_3$ starts to appear, and a point at which the absorption intensity of $H_2O$ starts to take a constant value after it increased. In order to find individual concentrations of NO and $NO_2$, what is necessary is to conduct the procedure specified in Embodiment 3-5.

In the stage (c), the concentration of CO can be measured. That is, combustion of CO under the existence of $O_2$ yields CO. Therefore, the concentration of CO contained in the gas removal tube can be calculated with the formula (12) by measuring the quantity of $O_2$ that is added up to either of two points: a point at which the absorption of CO disappears when $O_2$ are being added, and a point at which the absorption intensity of CO starts to take a constant value after it increased. Since for the quantity of $O_2$, only the quantity of addition should be measured, measurement can be done correctly. In Embodiment 3-6, when the $LiNbO_3$ bulk crystal 341 of a bulk length of 10 mm was used, the minimum detection concentration of $NO_2$ was 1 ppm at 100 Torr. When the waveguide of a length of 10 mm was used, the minimum detection concentration of $NO_2$ was able to be reduced to the order of 10 ppb.

Embodiment 3-7

With the use of a laser light source for generating mid-infrared light according to this invention, gases of $NO_x$, $CO_2$, CO, etc. each of which has absorption in the wavelength band of 2-3 μm can be detected by a remote operation. In Embodiment 3-7, the two-wavelength differential absorption LIDAR (for example, see Non-patent document 11) was used to detect environmental gases. The two-wavelength differential absorption LIDAR uses an absorption wavelength and a non-absorption wavelength of a measured gas. Since a LIDAR signal of the absorption wavelength suffers larger attenuation than that of the non-absorption wavelength, the concentration of a gas molecule can be measured using a signal difference between the two wavelengths.

In Embodiment 3-7, four kinds of gases, NO, $NO_2$, CO, and $CO_2$, are detected by the two-wavelength differential absorption LIDAR. The fundamental absorption wavelength, the wave number, the name of absorption, and the overtone absorption wavelength of each gas are as follows.

$CO_2$: 4.257 μm, 2349 cm$^{-1}$, anti-symmetry stretching vibration, overtone=2.129 μm CO: 4.666 μm, 2143 cm$^{-1}$, stretching vibration, overtone=2.333 μm NO: 5.330 μm, 1876 cm$^{-1}$, anti-symmetry stretching vibration, overtone=2.665 μm $NO_2$: 6.180 μm, 1618 cm$^{-1}$, anti-symmetry stretching vibration, overtone=3.090 μm In the measurement, it is required to perform measurement of two wavelengths at as close time points as possible in order to obtain accurate data. Since the laser light source according to this invention can find two targeted wavelengths instantaneously and it is necessary to prepare only a single period Λ for $LiNbO_3$ crystal, four kinds of gases in the wavelength band of 2-3 μm can be measured with an extreme rapidity.

Figure 20:
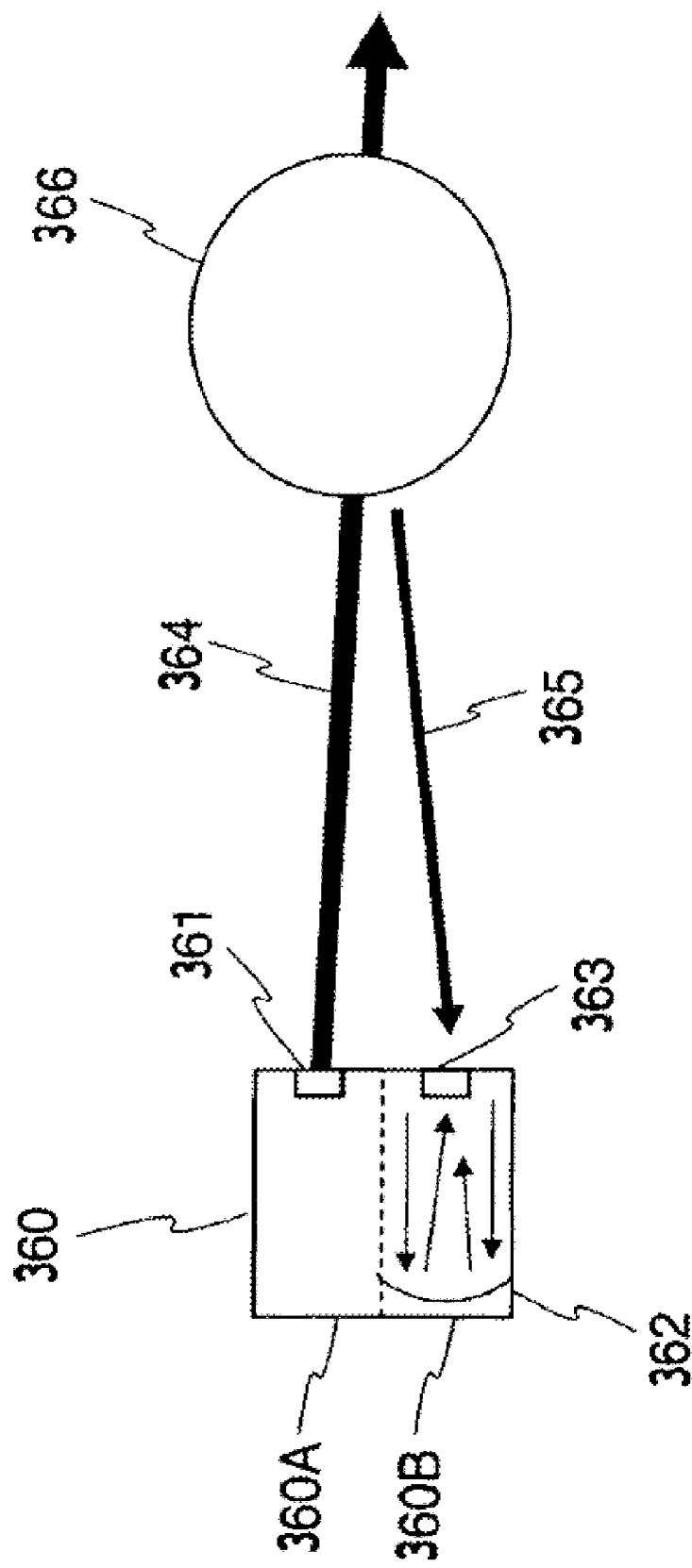
FIG. 20 is a view showing a measurement system of a two-wavelength differential absorption LIDAR according to Embodiment 3-7.

FIG. 20 shows a measurement system of a two-wavelength differential absorption LIDAR. A two-wavelength differential absorption LIDAR 360 consists of a laser beam emission unit 360A and a laser beam detection unit 360B. A laser light source included in the laser beam emission unit 360A uses a $LiNbO_3$ crystal waveguide of a device length of 10 mm. A period Λ of the periodically poled structure is specified as Λ=26 μm. The wavelength of the semiconductor laser 330 is specified in the 0.91-μm wavelength band and the wavelength of the semiconductor laser 331 is specified to be tunable between 1.28 μm and 1.46 μm wavelength. The laser beam emission unit 360A outputs mid-infrared light of a wavelength of 2-3 μm from a laser exist window 361 under suitable temperature adjustment.

Mid-infrared light 364 is emitted toward a detection gas 366. Scattered light 365 (Rayleigh scattering and Mie scattering) from the detection gas 366 is received by a reflector 362 inside the laser beam detection unit 360B. The focused beam is detected with a detector 363 that is a HgCdTe detector.

In the measurement, a non-absorption wavelength is set on 2-10 nm low wavelength side from the overtone absorption wavelength of the detection gas. The higher the intensity of the generated mid-infrared light, the longer the detectable length grows. Because of this, the intensity of the mid-infrared light is set to a high power of 10 mW. When the aforesaid four gases are diffused to a concentration of 1 ppm in a space three meters away from the detector (a spherical space of a diameter of one meter or more), absorption of all gases can be observed. If the gas concentration is increased to 10 ppm, the gases can be detected in a space to be measured ten meters away from the detector.

Embodiment 3-8

The laser light source for generating mid-infrared light according to this invention is also useful to detect pesticides remaining in agricultural products. CN group and $NO_2$ group contained in pesticides are typical examples of especially harmful functional groups. If these are detected successfully, a degree of the concentration of residual pesticides can be known. CN group and $NO_2$ group are included in fenpropathrin of the pyrethroid pesticide and 1-naphthyl-N-methylcarbamate of the carbamate pesticide. Absorption wavelengths are 4.44 μm for CN group (2250 cm-1, stretching vibration) and 6.15 μm for $NO_2$ group (1625 cm$^{-1}$, stretching vibration).

Figure 21:
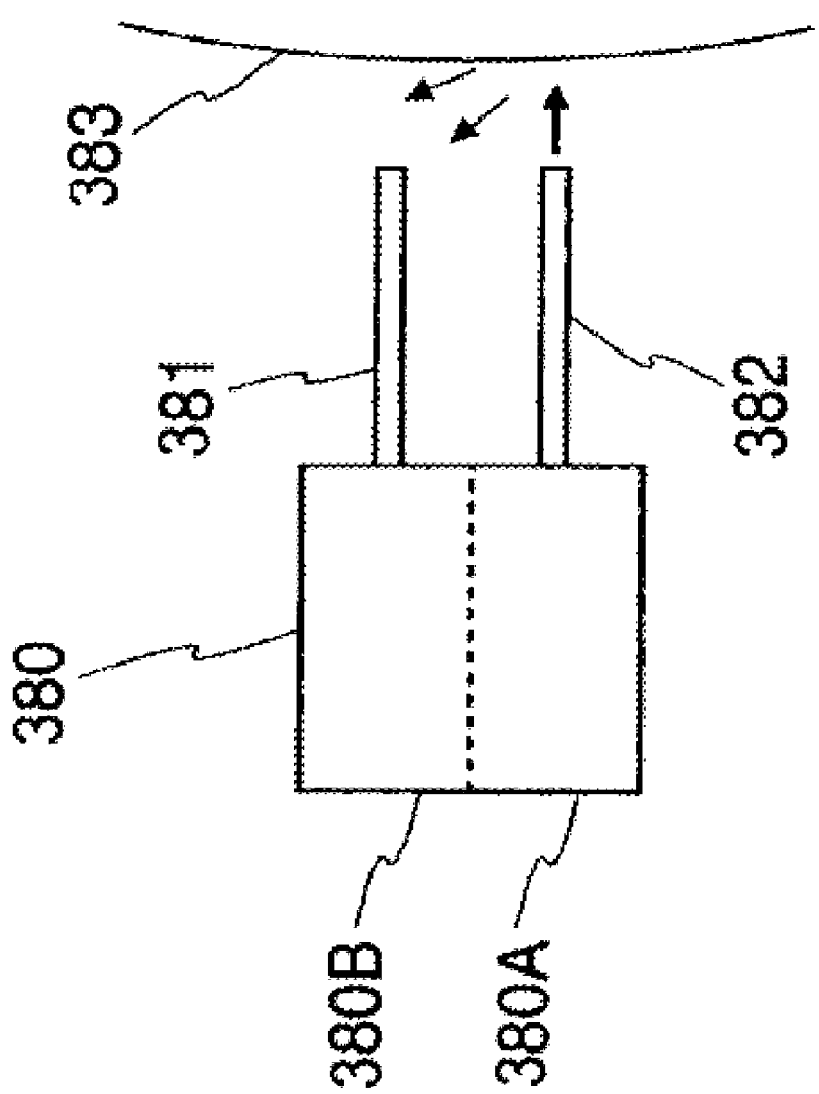
FIG. 21 is a view showing a measurement system of a pesticide residue measuring instrument according to Embodiment 3-8.

FIG. 21 shows a measurement system of a residual pesticide measuring instrument. A residual pesticide measuring instrument 380 consists of a laser beam emission unit 380A and a laser beam detection unit 380B. By means of optical fibers 381, 382 mounted on ends of the two units, a beam is emitted to an object under measurement consisting of agricultural products and its scattered beam is detected by the laser beam detection unit 380B. A HgCdTe detector and a PbSe detector are used for detectors installed inside the laser beam detection unit 380B. The laser light sources included in the laser beam emission unit 380A is under appropriate temperature adjustment, and uses the $LiNbO_3$ crystal waveguide that has a length of 10 mm and the periodically poled structure with a period Λ=26 μm. The wavelength of one of the semiconductor lasers was specified to be in the 0.91-μm wavelength band, and the other semiconductor laser 311 was specified to be tunable in a wavelength band of 1.3-1.65 μm.

Fenpropathrin and 1-naphthyl-N-methylcarbamate are applied on the skin of an apple under test (concentration of 1%), and mid-infrared light of a 10-mW power is irradiated onto this. As a result, overtone absorption of CN group at a wavelength 2.22 μm and overtone absorption of $NO_2$ group at a wavelength 3.08 μm were able to be observed sufficiently. The Embodiment 3-8 concludes that the existence of a plurality of functional groups can also be recognized with a $LiNbO_3$ crystal having a single period Λ in detecting residual pesticides.

Note that, if a functional group to be detected is only $NO_x$ group, this embodiment can also exhibit another advantage. That is, if setting the period of a $LiNbO_3$ crystal waveguide as Λ=27 μm (a period Λ=26 μm may be set, but a period Λ=27 μm is used for discussion in order to show the magnitude of the effect), the wavelength stability of the both semiconductor lasers used will improve when the absorption wavelength of the sample under test exists in a range of slightly larger than 3.0 μm, as described in Embodiment 3-4. So, even when using an optical system such that a reflective film on the facet of the semiconductor laser and the fiber Bragg grating of the optical fiber are removed, sufficient overtone absorption of $NO_2$ gas can be observed (incidentally, this effect can also be observed in the aforesaid detection of $NO_2$ gas similarly).

Fourth Embodiment

Figure 22:
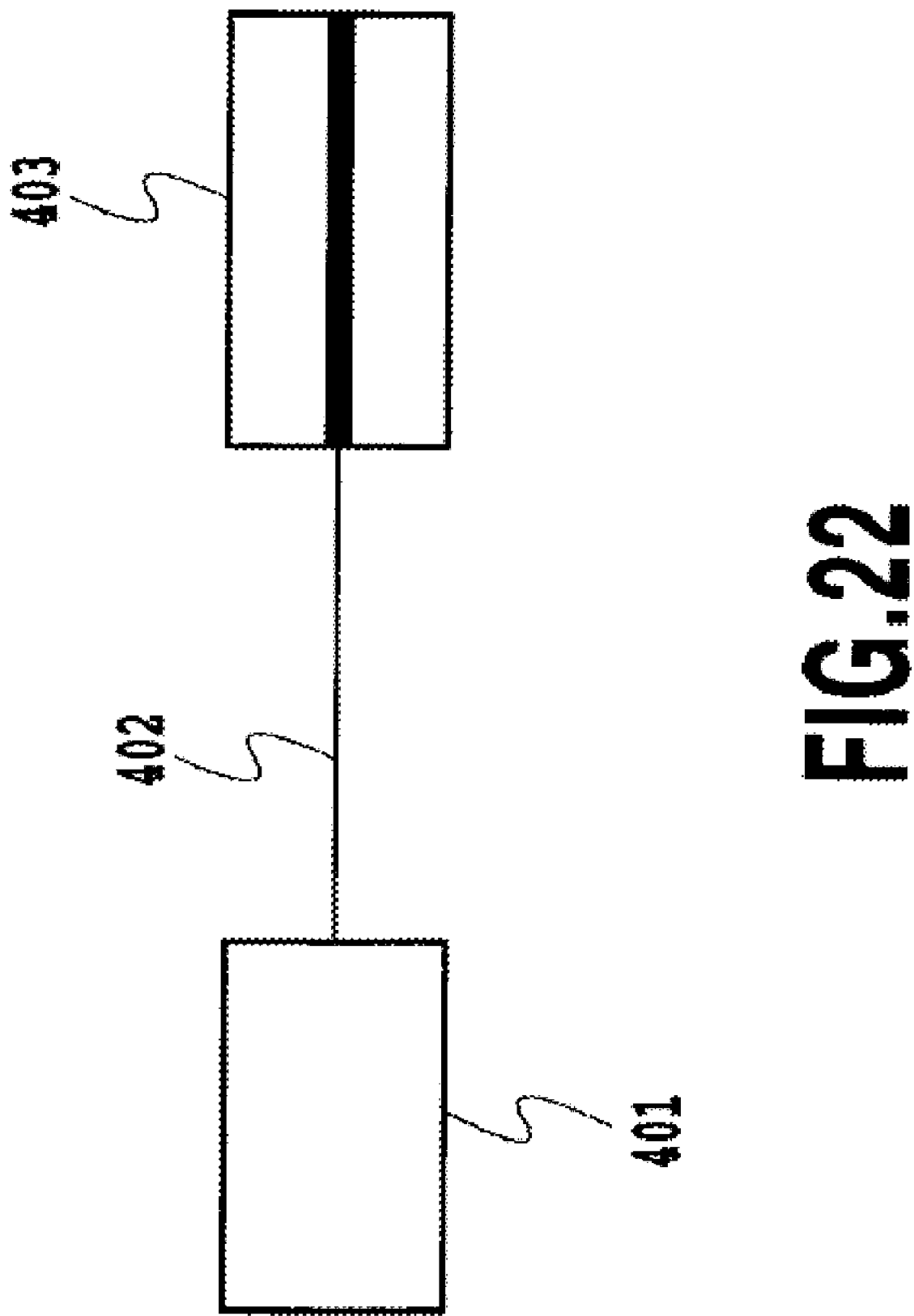
FIG. 22 is a block diagram showing a laser light source for generating a wavelength equal to an oxygen absorption line according to one embodiment of this invention.

FIG. 22 shows a laser light source for generating a wavelength of an oxygen-absorption line according to one embodiment of this invention. The laser light source for generating a wavelength of the oxygen absorption line comprises: a distributed feedback semiconductor laser module 401 that oscillates laser light of a wavelength twice a wavelength of one absorption line selected from oxygen absorption lines existing at wavelengths of 759 nm to 768 nm; an optical waveguide 403 having a second-order nonlinear optical effect; a polarization maintaining fiber 402 for connecting the semiconductor laser module 401 and one end of the optical waveguide 403 having the second-order nonlinear optical effect.

Since unlike the former examples, the semiconductor laser oscillates in the wavelength band of 1518-1536 nm that is twice the wavelength band of 759-768 nm, an indium phosphide system material is used for the semiconductor laser. It is known that devices based on indium phosphide hardly suffer so-called sudden death as compared to devices based on gallium arsenide, and the reliability over device life is high. Moreover, the wavelengths of 1518 to 1536 nm belong to the S-band and the C-band in the communication wavelength bands, so the manufacture of DFB lasers is technically easy, thanks to recent development in the optical communication field. Furthermore, a device as high-power as 40 mW can be produced.

In the semiconductor laser of the indium phosphide system, changing the temperature of a device or its injection current can vary the wavelength, and adopting a DFB type structure can perform stable wavelength scanning without mode jump. The laser light source converts laser light of a wavelength 1518-1536 nm to light of a wavelength 759-768 nm and outputted it using the second overtone generation based on the second-order nonlinear optical effect.

Here, the second-order nonlinear optical effect will be described. The nonlinear optical effect is an effect that occurs in a matter because electric polarization P in the substance has the high-order term of $E^2$ and $E^3$ in addition to a term that is proportional to the electric field E of light as follows.

$$P=\chi^{(1)}E+\chi^{(2)}E^2+\chi^{(3)}E^3+ \quad (15)$$

Especially, the second term is responsible for an effect that occurs strongly in a substance that lacks centro symmetry, yielding the following effects, representing three lights having different angular frequencies $\omega_1$, $\omega_2$, and $\omega_3$ that satisfy a relationship of $\omega_1+\omega_2=\omega_3$.

1) When light of $\omega_1$ and light of $\omega_2$ are inputted, light of $\omega_3$ is generated (sum frequency generation).

2) In the case where $\omega_1$ and $\omega_2$ are the same angular frequency at the time of sum frequency generation, a second overtone is generated.

3) When light of $\omega_1$ and light of $\omega_3$ are inputted, light of $\omega_2$ ($=\omega_3-\omega_1$) is generated (difference frequency generation).

That is, the wavelength of an input laser beam can be converted to another wavelength.

The efficient wavelength converter has been realized by reversing polarization of a second-order nonlinear optical material periodically. This structure is such that an influence of refractive index dispersion due to a material is solved by reversing the polarization periodically to match phases of input light and converted light in a quasi manner. As an example using this principle, there is known a wavelength converter such that polarization of, for example, lithium niobium oxide that is a second-order nonlinear optical material is reversed periodically and a waveguide is formed therein by proton exchange (see Non-patent document 12). It has been demonstrated that a lithium niobium oxide optical waveguide having such a periodically poled structure can generate a second overtone whose energy reaches 90% or more of that of the fundamental light.

The optical waveguide having such the second-order nonlinear optical effect involves a life-related problem that the efficiency of the second overtone generation decreases by a photorefractive effect. Since this problem does not occur with light of wavelengths of 1518 nm to 1536 nm, it occurs depending on the light intensity of wavelengths of 759 nm to 768 nm that is a second overtone wave. However, it is known that the efficiency decrease can be avoided by increasing the temperature of an optical waveguide having the second-order nonlinear optical effect from 50° C. to about 100° C. or by using a second-order nonlinear optical material to which zinc or magnesium was doped (for example, see Non-patent document 13); therefore, it is easy to obtain a long-life optical waveguide.

Optical waveguides having such the second-order nonlinear optical effect exhibit the effect strongly to light that is polarized in a specific direction with reference to a crystal orientation. For example, it is the z-axis direction in lithium niobium oxide. The semiconductor laser oscillates with a certain polarization with reference to its substrate. Therefore, when the semiconductor laser module 401 and the optical waveguide 403 having the second-order nonlinear optical effect are connected using an optical fiber, it is preferable to use the polarization maintaining fiber 402 in order to suppress variation in the direction of polarization of incident light to the optical waveguide. Incidentally, if the semiconductor laser module 401 is connected using an optical fiber that is not a polarization maintaining fiber and a polarization controlling element is intercalated in the optical fiber, second overtone generation is possible. However, it is difficult to generate a second overtone stably in a long period because polarization in the optical fiber may fluctuate due to a change in external environments, such as temperature.

Figure 23:
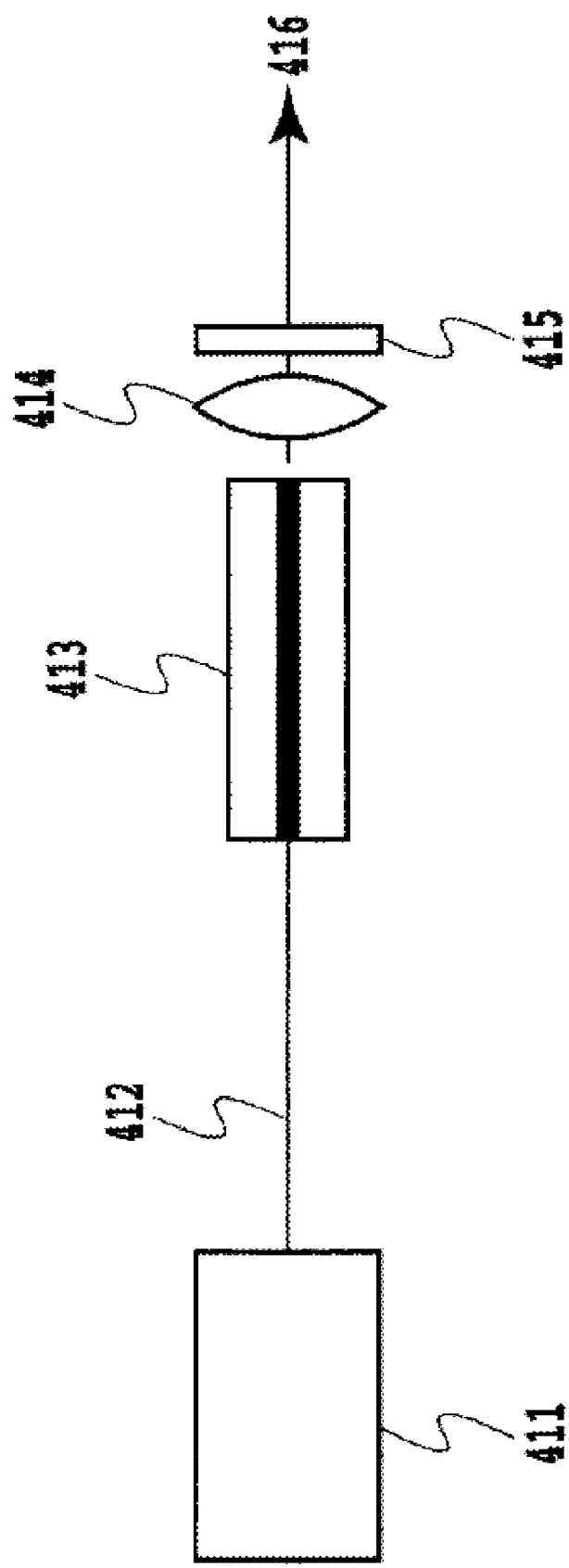
FIG. 23 is a block diagram showing a laser light source equipped with a lens and a filter for output.

FIG. 23 shows a laser light source equipped with a lens and a filter for output. That is, in addition to the laser light source in FIG. 22, the other end of an optical waveguide 413 having the second-order nonlinear optical effect is equipped with a lens for collimating an emitted beam and a filter that allows beams of wavelengths of 759 nm to 768 nm to pass through but does not allow beams of wavelengths of 1518 nm to 1536 nm among the emitted beams to pass through. Thus, in the wavelengths of 759 nm and 768 nm that are oxygen absorption lines, a beam for performing stable wavelength scanning without mode jump can be extracted.

Figure 24:
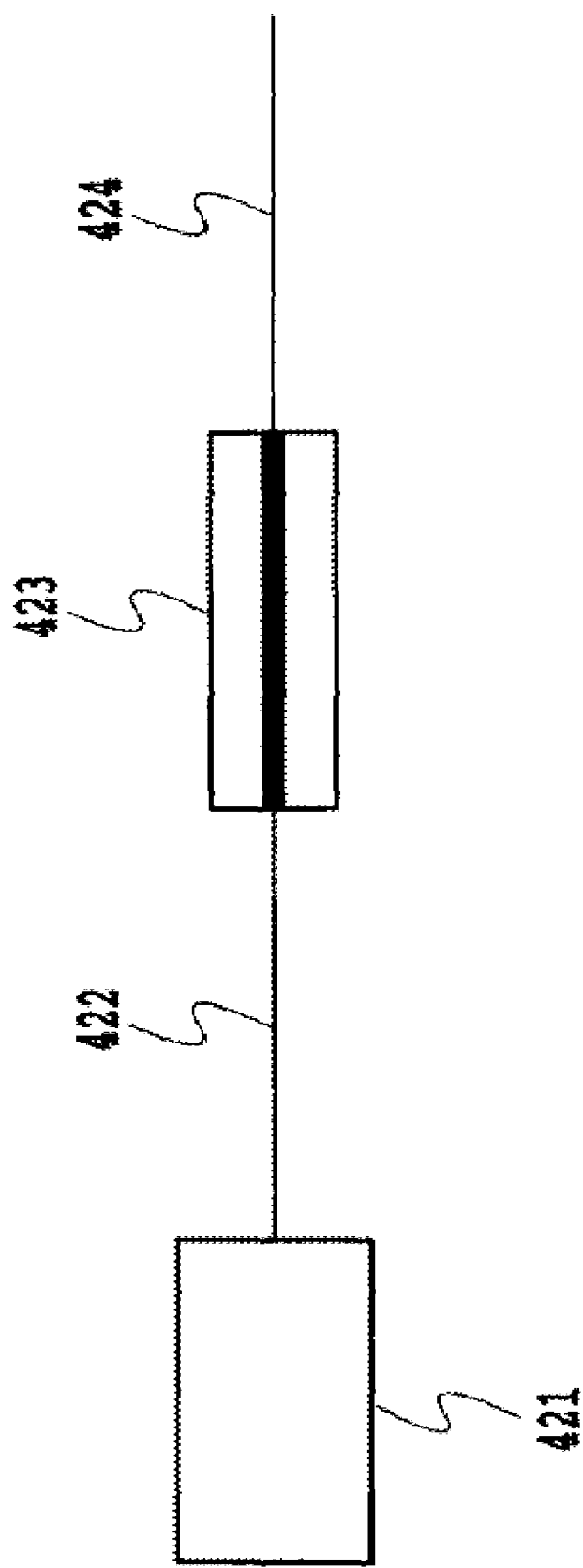
FIG. 24 is a block diagram showing a laser light source equipped with an optical fiber for output.

FIG. 24 shows a laser light source equipped with an optical fiber for output. In place of the embodiment in FIG. 23, an optical fiber 424 is connected to the other end of an optical waveguide 423 having the second-order nonlinear optical effect. If the optical fiber 424 is of a structure capable of guiding light of wavelengths of 768 nm to 759 nm in a single mode, only light of wavelengths of 759 nm to 768 nm that are the oxygen absorption lines can be taken out just by adding the optical fiber 424 a slightest bend. This is because light of wavelengths of 1518 nm to 1536 nm propagates in the optical fiber as a wide mode, and consequently, if there is a part that suffers a slightest bend, such light is scattered in that part and attenuated in the optical fiber 424.

As described above, it becomes possible to provide a high-power, long-life laser light source that can output a laser beam of wavelengths of 759 nm to 768 nm that are the oxygen absorption lines using second overtone generation based on the second-order nonlinear optical effect of the optical waveguide, and perform stable wavelength scanning without mode jump.

Embodiment 4-1

Figure 25:
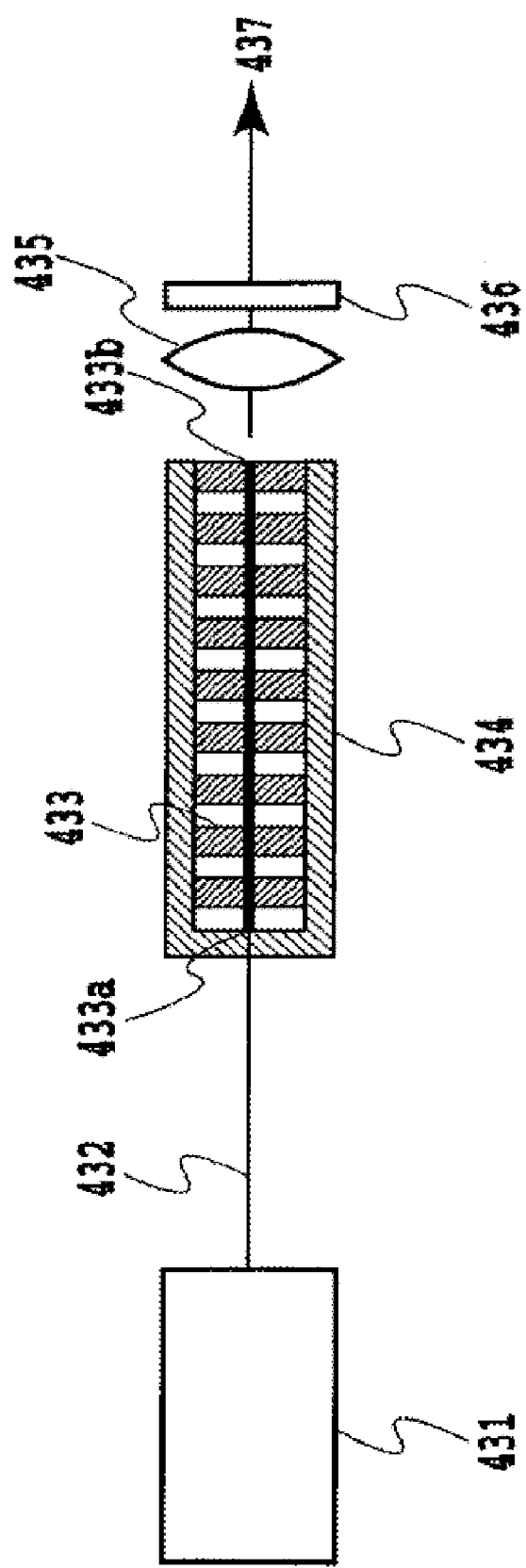
FIG. 25 is a block diagram showing a laser light source according to an embodiment 4-1.

FIG. 25 shows a laser light source according to an embodiment 4-1. The laser light source according to the embodiment 4-1 comprises: a distributed feedback semiconductor laser module 431 for oscillating a laser beam; an optical waveguide 433 having the second-order nonlinear optical effect; and a polarization maintaining fiber 432 that connects the semiconductor laser module 431 and one end of the optical waveguide having the second-order nonlinear optical effect. At the other end 433b of the optical waveguide 433 having the second-order nonlinear optical effect, a lens 435 for collimating an emitted beam and a filter 436 that does not allow a beam near 1526 nm to pass through but allows a beam near 763 nm to pass through among emitted beams.

The semiconductor laser module 431 oscillates a laser beam near 1526.08 nm that is twice the 763.04-nm wavelength that is one of oxygen absorption lines and is emitted from the polarization maintaining fiber 432. The semiconductor laser module 431 has an internal Peltier device (not illustrated), which enables the temperature of the device to be varied. Moreover, the semiconductor laser module has an internal isolator (not illustrated), which prevents a reflected beam from a facet of the optical waveguide etc. from causing an adverse effect on laser oscillation.

For a waveguide 433 having the second-order nonlinear optical effect, the periodically poled structure is formed on a lithium niobium oxide substrate. The formation of the waveguide is done using a method according to the fifth embodiment or an annealed proton exchange method. A coating that is non-reflective to a wavelength of 1526 nm is formed on one end 433a of the optical waveguide 433. Moreover, a coating that becomes non-reflective to a wavelength of 763 nm is formed on the other end 433b of the optical waveguide 433. Under the optical waveguide 433, disposed is a Peltier device that keeps the temperature of the optical waveguide 433 at 90° C. so that the second overtone generation may become most efficient at the 1526.08-nm wavelength of the incident beam on the optical waveguide 433.

When the semiconductor laser module 431 was set at 25° C. and operated at the 1526.08-nm wavelength to deliver an output of 30 mW, light of a wavelength 763.04 nm and an output of 5 mW is observed as an output beam 437. The output beam 437 was observed while the temperature of the semiconductor laser module 431 was varied from 24° C. to 26° C. continuously. The wavelength varied from 762.99 nm to 763.09 nm continuously, and any phenomenon like mode jump was not observed. The light intensity of the output beam 437 varied from 4.7 mW to 5.0 mW, showing a stable operation. This operation was performed continuously through one year, and neither decrease in the output nor mode jump was observed.

Embodiment 4-2

Figure 26:
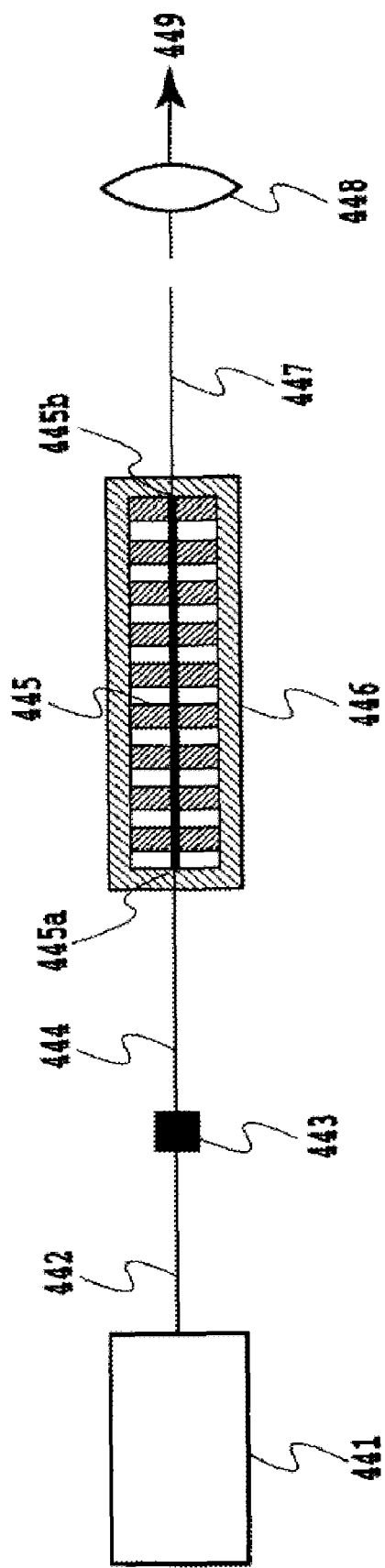
FIG. 26 is a block diagram showing a laser light source according to an embodiment 4-2.

FIG. 26 shows a laser light source according to an embodiment 4-2. The laser light source according to the embodiment 4-2 comprises: the distributed feedback semiconductor laser module 401 that oscillates a laser beam; an optical waveguide 445 having the second-order nonlinear optical effect; the polarization maintaining fiber 402 for connecting a semiconductor laser module 441 and one end 445a of the optical waveguide 445 having the second-order nonlinear optical effect; and an optical connector. An optical fiber 447 is connected to the other end 445b of the optical waveguide 445 having the second-order nonlinear optical effect, and a lens 449 for collimating an emitted beam is disposed near the optical fiber 447.

For the semiconductor laser module 441, the same module as that of the embodiment 4-1 was used. For the waveguide 445 having the second-order nonlinear optical effect, the periodically poled structure is formed on a Zn-doped lithium niobium oxide substrate, and the waveguide is formed using a method according to the fifth embodiment or the annealed proton exchange method. A coating that is non-reflective to the 1526-nm wavelength is formed on one end 445a of the optical waveguide 445, to which a polarization maintaining fiber 444 that guides a single mode to light near the 1526-nm wavelength is connected. Moreover, a coating that is non-reflective to the 763-nm wavelength is formed on the other end 445b of the optical waveguide 445, to which the polarization maintaining fiber 447 that guides a single mode to light near the 763-nm wavelength is connected.

Under the optical waveguide 445, disposed is a Peltier device 446 for temperature control, which keeps the temperature of the optical waveguide 445 at 25.0° C. so that the second overtone generation may become most efficient at the 1526.08-nm wavelength of the incident light on the optical waveguide 445. An optical fiber 442 and the optical fiber 444 are connected with a connector 443, and an optical output of the optical fiber 447 is collimated into a parallel beam with a lens 448.

When the semiconductor laser module 441 was set at 25° C. and operated at the 1526.08-nm wavelength delivering an output of 30 mW, light of a wavelength 763.04 nm and an output of 7 mW was observed as an output beam 449. The output beam 449 was observed while the temperature of the semiconductor laser module was being varied from 24° C. to 26° C. continuously and the temperature of the optical waveguide 445 was being varied from 24° C. to 26° C. continuously by the Peltier device 446. The wavelength varied from 762.99 nm to 763.09 nm continuously, the light intensity of the output beam 449 varied from 6.9 mW to 7.0 mW, showing an extremely stable operation.

At this time, light of the 1526-nm wavelength that passed through the laser light source without being converted into the second overtone was below an observation limit in the output beam 449. This is because light in the vicinity of 1526 nm propagates as a wider mode in the optical fiber 447, and if there is a part that suffers a slightest bend, the light is scattered at that part and attenuates in the optical fiber 447. Incidentally, a filter for removing the 1526-nm wavelength may be installed downstream the lens 448 for safety's sake. Although the polarization maintaining fiber was connected using the connector 443 in the embodiment 4-2, it goes without saying that connection may be done by fusion splice.

In this embodiment, paying attention to 763.04 nm that is one of oxygen absorption lines, a semiconductor laser is selected and the laser light source is constructed with this laser. Alternatively, in order to generate other absorption line existing between 759 nm and 768 nm, for example 760.4 nm, the 1520.8-nm wavelength that is twice the 760.4-nm wavelength may be selected.

Although in this embodiment, a waveguide having the periodically poled structure was used for the optical waveguide having the second-order nonlinear optical effect, the same effect can be obtained using other phase matching method. Moreover, for the substrate, lithium niobium oxide or Zn-doped lithium niobium oxide was used. However, the same effect can be obtained even if using a mixed crystal of lithium niobium oxide and lithium tantalum oxide, the mixed crystal to which a minute quantity of an element is doped, or other second-order nonlinear optical material. Furthermore, although the method according to the fifth embodiment or the annealed proton exchange method was used as a method for manufacturing a waveguide, naturally the same effect can be obtained even with the use of a metal diffused waveguide, such as Ti diffusion, a ridge waveguide, an embedded waveguide, or the like.

It is needless to say that a waveguide structure may be altered for both ends and their neighborhoods of the optical waveguide having the second-order nonlinear optical effect so that it becomes easy to couple the beam to optical fibers to be connected to the respective facets, or so that a shape of the beam when being emitted to space becomes optimal. Moreover, although the isolator was built in the semiconductor laser module, the reflected return light may be prevented by providing anti-reflection coatings on facets of the optical waveguide having the second-order nonlinear optical effect, cutting aslant the optical waveguide having the second-order nonlinear optical effect and arranging optical fibers or lenses accordingly, or combining these measures.

Fifth Embodiment

Next, a method for forming a waveguide in a nonlinear optical crystal will be described. This embodiment uses a ridge-type waveguide using a wafer-direct-bonded substrate. In the wafer-direct-bonding method, a $LiNbO_3$ substrate having the periodically poled structure matched to an operating wavelength and a substrate whose surface has been treated are bonded directly at room temperature without an intermediate of an adhesive, and the substrates are subjected to annealing. For a waveguide, the periodically poled structure of the bonded substrate is ground or made to be a thin film. Subsequently a ridge-type waveguide is formed on the bonded and thinned substrate using a dicing saw.

As a problem that the $LiNbO_3$ substrate has, improvement in optical-damage resistance exists. The optical damage is a phenomenon in which light that is made to enter the waveguide excites carriers from defects existing in a crystal, subsequently the carriers are trapped in the crystal, which induces refractive index change (photorefractive effect), and this change causes a shift in an operating wavelength. Since an operating wavelength band of the waveguide is as narrow as 1 nm due to a $LiNbO_3$ substrate, in case an optical damage exists, the power of output beam will decrease considerably, or even no power will be outputted. In the waveguide element formed by applying the proton exchange method on a non-doped $LiNbO_3$ substrate, it is necessary to set the operating temperature of the waveguide element at 100° C. or more in order to realize sufficient optical damage resistance. However, there is a problem that, because of proton re-diffusion caused by this heating, long-term stability cannot be maintained. A waveguide element that is formed by applying the proton exchange method on a $LiNbO_3$ substrate to which Mg or Zn was doped instead of a non-doped $LiNbO_3$ substrate exhibits a certain degree of improvement in the optical damage resistance. However, the waveguide device needs to be heated to 50° C. or more.

Here, using the wavelength conversion efficiency, power Pa of the sum frequency light or the difference frequency light, is expressed by the following formula $$P = \eta L^2 P_1 P_2 / 100,$$

and power Pb of the second overtone is expressed by $$Pb = \eta L^2 P_3^2 / 100,$$

where $\eta$ is the efficiency per unit length (%/W/cm$^2$), L is device length, and $P_1$, $P_2$, and $P_3$ are output beam powers of excitation lasers.

In this embodiment, the laser light source can operate at wavelengths except for the wavelength band for optical communications, and deliver stable output of more than 10 mW by combining with a high-power semiconductor laser of about 10-100W. Thus, the laser light source can generate a laser beam of an arbitrary wavelength in the wavelength band of 450 nm to 5 μm where LiNbO$_3$ is transparent.

Embodiment 5-1

Figure 27:
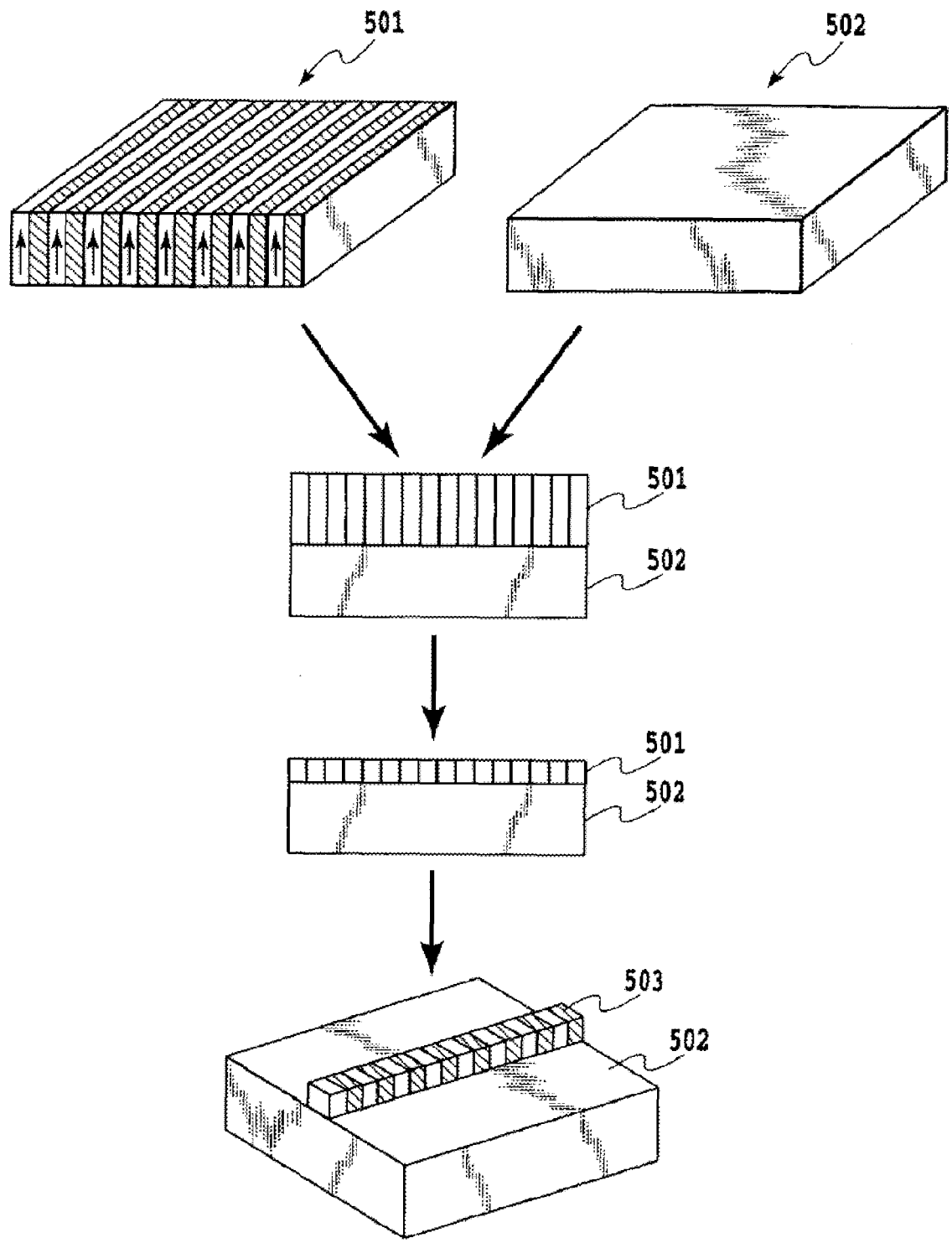
FIG. 27 is a view showing a method for manufacturing a single-mode ridge-type waveguide.

FIG. 27 shows a method for manufacturing a single-mode ridge-type waveguide. A first substrate 501 is Z-cut Zn-doped LiNbO$_3$ substrate in which the periodically poled structure is formed in advance, and a second substrate 502 is Z-cut Mg-doped LiNbO$_3$ substrate. Each of the substrates 501,502 is a 3-inch wafer whose both surfaces are optical-polished and whose substrate thickness is 300 μm. The surfaces of the first substrate 501 and of the second substrate 502 were made hydrophilic by usual acid cleaning or alkali cleaning, and subsequently the substrates 501, 502 are superposed in clean atmosphere. The superposed substrates 501,502 were put into an electric furnace and subjected to diffusion bonding by heat-treating it at 400° C. for 3 hours (first process). The bonded substrates 501,502 were void-free, and when being returned to room temperature, cracks etc. did not occur in these substrates.

Next, the first substrate 501 was treated by grinding until its thickness became 5 to 10 μm using grinding equipment whose turn table for grinding was under control in terms of flatness. After grinding process, the substrates 501, 502 are subjected to polishing to obtain a specular polished surface (second process). The thickness of the substrates was measured with an optical thickness measuring instrument. Uniform thickness in the submicron range was obtained for almost the whole surface, except for the periphery of the 3-inch wafer. Thus, a thin film substrate suitable for formation of a waveguide was able to be manufactured. Incidentally, an X-cut Zn-doped LiNbO$_3$ substrate may be used as the first substrate 501, and an X-cut Mg-doped LiNbO$_3$ substrate may be used as the second substrate 502.

A waveguide pattern was formed on the surface of the manufactured thin-film substrata by a usual photolithographic process. Subsequently, the substrate was set in a dry etching apparatus, and the substrate surface was etched using CF$_4$ gas as an etching gas, whereby a core of a width of 6-20 μm was formed to manufacture a ridge-type waveguide (third process). A waveguide element of the nonlinear optical crystal of a length of 10-60 mm can be obtained by cutting out a ridge-type waveguide from the wafer and polishing waveguide facets.

Embodiment 5-2

The first substrate 501 is a Z-cut Zn-doped LiNbO$_3$ substrate in which the periodically poled structure is formed in advance, and the second substrate 502 is a Z-cut LiTaO$_3$ substrate. Each of the substrates 501,502 is a 3-inch wafer whose both surfaces were optical-polished, having a thickness of 300 μm. The surfaces of the first substrate 501 and of the second substrate 502 were made hydrophilic by usual acid cleaning or alkali cleaning, and subsequently the substrates 501, 502 were superposed in clean atmosphere. The superposed substrates 501,502 were put into an electric furnace and subjected to diffusion bonding by heat-treating it at 400° C. for 3 hours (first process). The bonded substrates 501, 502 were void-free, and when being returned to room temperature, cracks etc. did not occur in these substrates.

Next, the adhered substrates 501, 502 were treated by polishing using grinding equipment whose turn table for grinding was under control in terms of flatness until the thickness of the first substrate 501 became 6-10 μm. After the grinding, the substrates 501, 502 was subjected to polishing to obtain a specular polished surface (second process). The thickness of the substrates was measured with an optical thickness measuring instrument. Uniform thickness in the submicron range was obtained for almost the whole surface, except for the periphery of the 3-inch wafer. Thus, a thin film substrate suitable for formation of a waveguide was able to be manufactured. Incidentally, an X-cut Zn-doped LiNbO$_3$ substrate may be used as the first substrate 501, and an X-cut LiTaO$_3$ substrate may be used as the second substrate 502.

A waveguide pattern was formed on the surface of the manufactured thin-film substrata by a usual photolithographic process. Subsequently, the substrate was set in a dry etching apparatus, and the substrate surface was etched using CF$_4$ gas as an etching gas, whereby a core of a width of 6-20 μm was formed to manufacture a ridge-type waveguide (third process). A waveguide element of the nonlinear optical crystal of a length of 10-60 mm can be obtained by cutting out a ridge-type waveguide from the wafer and polishing waveguide facets.

Embodiment 5-3

The first substrate 501 is a LiNbO$_3$ substrate in which the periodically poled structure is formed in advance, and the second substrate 502 is a quartz substrate. The thermal expansion coefficient of quartz in an in-plane direction perpendicular to Z-axis is 13.6×10$^{-6}$/K, which is close to the thermal expansion coefficient of LiNbO$_3$, and the refractive index of quartz is 1.53, which is smaller than the refractive index of LiNbO$_3$, 2.1. Consequently, this combination is suitable for manufacture of a waveguide. By the same manufacture method as that of the embodiment 5-1, a waveguide element of a nonlinear optical crystal can be obtained.

A Mg-doped LiNbO$_3$ substrate, a Sc-doped LiNbO$_3$ substrate, an In-doped LiNbO$_3$ substrate, a LiTaO$_3$ substrate, a LiNb$_x$Ta$_{1-x}$O$_3$ substrate, a KNbO$_3$ substrate, a KTiNbO$_3$ substrate, etc. may be used as the first substrate 501, instead of the Zn-doped LiNbO$_3$ substrate.

Embodiment 5-4

In order to form a waveguide of an embodiment 5-4, precision grinding by a dicing saw is performed on the substrate that is manufactured up to the second process of the embodiment 5-1. That is the ground substrate is set in a dicing saw, and a ridge-type waveguide having a core of a width of 6 μm is manufactured by precision machining using a diamond blade whose particles are 4 μm in diameter (third process). A waveguide element made of the nonlinear optical crystal of a length of 10-60 mm can be obtained by cutting out a ridge-type waveguide and optical polishing the facets of the waveguide. Incidentally, the substrate manufactured in the embodiment 5-2 or in the embodiment 5-3 may be used.

According to this embodiment, the accuracy in refractive index measurement at the sodium D line can be improved by about two orders of magnitude compared to the present state. Therefore, quality control of foods or medicines can be improved largely, and in addition the safety can be improved largely by increasing monitoring accuracy for foreign matters and inclusion of poisons. Moreover, regarding a substance whose relationship between the refractive index and the density is known, it becomes possible to obtain the density form the measurement of the refractive index, and the accuracy in this density measurement is also enhanced remarkably.

Moreover, according to this embodiment, a compact and economical laser microscope, flow cytometer, etc. can be realized by adopting an energy-efficient, compact, and low-consumption laser light source.

Furthermore, the laser light source for generating mid-infrared light according to this embodiment can detect environmental gases accurately, and can be applied to a measurement instrument for detecting pesticides that remain in agricultural products.

Even further, the laser light source can be used as a laser light source that is used for an oxymeter and outputs a laser beam of wavelengths of 759 nm to 768 nm that are oxygen absorption lines.

What is claimed is:

1. A laser light source comprising:
   a first laser for generating a laser beam of a wavelength $\lambda_1$;
   a second laser for generating a laser beam of a wavelength $\lambda_2$; and
   a nonlinear optical crystal that uses the laser beam of the wavelength $\lambda_1$ and the laser beam of the wavelength $\lambda_2$ as inputs and outputs a coherent beam having a wavelength $\lambda_3$ of a difference frequency that satisfies a relationship of $1/\lambda_1 - 1/\lambda_2 = 1/\lambda_3$, and wherein:
   the wavelength $\lambda_1$ is selected in the range of 0.9-1.0 µm,
   the nonlinear optical crystal is $LiNbO_3$ having a periodically poled structure of a single period and satisfies a relation as follows:

$$\frac{\sin^2\left(\frac{\Delta k l}{2}\right)}{\left(\frac{\Delta k l}{2}\right)^2} \geq 0.5 \text{ where}$$

-continued
$$\Delta k = k_3 - k_1 + k_2 + \frac{2\pi}{\Lambda}, k_i = \frac{2\pi}{\lambda_i} n_i,$$

and l is a length of the nonlinear optical crystal, refractive indices of the wavelengths $\lambda_1$, $\lambda_2$, and $\lambda_3$ are represented by $n_1$, $n_2$, $n_3$, respectively, and $\Lambda$ is the single period, and the wavelength $\lambda_3$ of a difference frequency varies between 3.1 µm and 2.0 µm when the wavelength $\lambda_2$ varies between 1.3 µm and 1.8 µm.

2. The laser light source according to claim 1, wherein the nonlinear optical crystal has a waveguide structure.

3. The laser light source according to claim 1, further comprising:
   two polarization maintaining fibers coupled to outputs of the first and second lasers, respectively; and
   a multiplexer for multiplexing outputs of the two polarization maintaining fibers and coupling a multiplexed output to the nonlinear optical crystal.

4. The laser light source according to claim 3, wherein the first and second lasers are semiconductor lasers, and at least one of the two polarization maintaining fibers has a fiber Bragg grating.

5. The laser light source according to claim 1, further comprising:
   a temperature controlling device thermally coupled to the nonlinear optical crystal; and
   a temperature control circuit for controlling the temperature of the nonlinear optical crystal by controlling the temperature controlling device.

6. An optical absorption analyzer comprises
   a laser light source as recited in claim 1, the laser light source being a laser beam emitting means,
   a gas cell, and
   laser beam detecting means, wherein the optical absorption analyzer measures a gas concentration optically.

7. A two-wavelength differential absorption LIDAR comprises
   a laser light source as recited in claim 1, the laser light source being a two-wavelength light source for outputting two laser beams having an absorption wavelength and a non-absorption wavelength, respectively, wherein the two-wavelength differential absorption LIDAR measures a gas concentration using an intensity difference between scattered beams of the respective laser beams from the measured gas.

* * * * *